US009474764B2

(12) United States Patent
Van Der Beek et al.

(10) Patent No.: US 9,474,764 B2
(45) Date of Patent: Oct. 25, 2016

(54) INFANT NUTRITION FOR IMPROVING FATTY ACID COMPOSITION OF BRAIN MEMBRANES

(75) Inventors: Eline Marleen Van Der Beek, Wageningen (NL); Marieke Abrahamse-Berkeveld, Heteren (NL); Annemiek Lidewij Schipper, Leusden (NL); Gelske Speelmans, Wageningen (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 13/635,389

(22) PCT Filed: Mar. 17, 2011

(86) PCT No.: PCT/NL2011/050187
§ 371 (c)(1),
(2), (4) Date: Nov. 28, 2012

(87) PCT Pub. No.: WO2011/115490
PCT Pub. Date: Sep. 22, 2011

(65) Prior Publication Data
US 2013/0071446 A1 Mar. 21, 2013

(30) Foreign Application Priority Data
Mar. 17, 2010 (NL) ................ PCT/NL2010/050142

(51) Int. Cl.
| A61K 31/685 | (2006.01) |
| A23D 7/01 | (2006.01) |
| A23D 9/013 | (2006.01) |
| A23D 9/05 | (2006.01) |
| A23L 1/00 | (2006.01) |
| A23L 1/29 | (2006.01) |
| A23L 1/30 | (2006.01) |
| A61K 31/201 | (2006.01) |
| A61K 31/683 | (2006.01) |
| A61K 9/00 | (2006.01) |
| A61K 31/202 | (2006.01) |

(52) U.S. Cl.
CPC .............. *A61K 31/685* (2013.01); *A23D 7/011* (2013.01); *A23D 9/013* (2013.01); *A23D 9/05* (2013.01); *A23L 1/0032* (2013.01); *A23L 1/296* (2013.01); *A23L 1/3006* (2013.01); *A23L 1/3008* (2013.01); *A61K 9/0087* (2013.01); *A61K 31/201* (2013.01); *A61K 31/202* (2013.01); *A61K 31/683* (2013.01); *A23V 2002/00* (2013.01)

(58) Field of Classification Search
None
See application file for complete search history.

(56) References Cited

U.S. PATENT DOCUMENTS

| 5,709,888 | A | 1/1998 | Gil et al. |
| 2002/0004527 | A1* | 1/2002 | Auestad et al. ............. 514/560 |
| 2003/0104078 | A1 | 6/2003 | Barrett-Reis et al. |
| 2004/0062820 | A1 | 4/2004 | Lasekan et al. |
| 2005/0037089 | A1 | 2/2005 | Jobbins |
| 2005/0214392 | A1 | 9/2005 | McPeak et al. |
| 2006/0188614 | A1 | 8/2006 | Shapira |
| 2006/0210697 | A1 | 9/2006 | Mower |
| 2007/0073193 | A1 | 3/2007 | Park |
| 2007/0073194 | A1 | 3/2007 | Chen et al. |
| 2008/0064656 | A1* | 3/2008 | Van Tol ..................... 514/54 |
| 2008/0292724 | A1 | 11/2008 | Joseph |
| 2009/0011075 | A1* | 1/2009 | Shulman et al. ................. 426/2 |
| 2009/0186803 | A1* | 7/2009 | Zwijsen et al. ................... 514/2 |
| 2011/0097438 | A1 | 4/2011 | Van Baalen et al. |
| 2011/0206743 | A1 | 8/2011 | Van Baalen et al. |
| 2011/0217411 | A1 | 9/2011 | Van Der Beek et al. |
| 2011/0300204 | A1 | 12/2011 | Van der Beek et al. |
| 2011/0300225 | A1 | 12/2011 | Van Der Beek et al. |
| 2013/0052297 | A1 | 2/2013 | Van De Heijning et al. |

FOREIGN PATENT DOCUMENTS

| EP | 0 333 288 A1 | 9/1989 |
| EP | 1 252 824 A2 | 10/2002 |
| EP | 1 800 675 A1 | 6/2007 |
| EP | 2 305 049 A1 | 4/2011 |
| JP | 2001-158736 | 6/2001 |
| SU | 1084006 A | 4/1984 |
| WO | WO-03/005836 A2 | 1/2003 |
| WO | WO-2005/007373 A1 | 1/2005 |
| WO | WO-2005/051091 A1 | 6/2005 |
| WO | WO-2005/051092 A2 | 6/2005 |
| WO | WO-2006/052134 A2 | 5/2006 |
| WO | WO-2006/094995 A1 | 9/2006 |
| WO | WO-2006/114790 A2 | 11/2006 |
| WO | WO-2007/073192 A2 | 6/2007 |
| WO | WO-2007/073193 A2 | 6/2007 |
| WO | WO-2007/073194 A2 | 6/2007 |
| WO | WO-2007/097523 A2 | 8/2007 |

(Continued)

OTHER PUBLICATIONS

InFat™—The premium choice for infant formula—closer to mother's milk. Nov. 2009. AAK Magazine. <http://www.aak.com/Global/FoodIngredients/Babyfood/Infat_the_premium.pdf> accessed Aug. 19, 2013.*
Alan Lucas MB, MD. "Long-Term Programming Effects of Early Nutrition—Implications for the Preterm Infant". Journal of Perinatology (2005) 25, S2-S6.*
U.S. Appl. No. 13/635,381, filed Mar. 17, 2011, Eline Marteen Van Der Beek et al.
Benoit et al., "Phospholipid Species and Minor Sterols in French Human Milks," Food Chemistry, 120:684-691 (2010).

(Continued)

*Primary Examiner* — David J Blanchard
*Assistant Examiner* — Sarah Chickos
(74) *Attorney, Agent, or Firm* — Foley & Lardner LLP; Sunit Talapatra

(57) ABSTRACT

The present invention relates to infant nutrition, in particular to infant nutrition comprising special lipid globules for improvement of the fatty acid composition in brain membranes.

22 Claims, No Drawings

(56) References Cited

FOREIGN PATENT DOCUMENTS

| | | | |
|---|---|---|---|
| WO | WO-2008/005033 A1 | 1/2008 | |
| WO | WO-2008/054192 A1 | 5/2008 | |
| WO | WO-2008/081934 A1 | 7/2008 | |
| WO | WO-2009/051502 A1 | 4/2009 | |
| WO | WO-2009/057121 A1 | 5/2009 | |
| WO | WO-2009/066685 A1 | 5/2009 | |
| WO | WO-2009/138680 A2 | 11/2009 | |
| WO | WO-2009/154448 A1 | 12/2009 | |
| WO | WO-2010/027258 A1 | 3/2010 | |
| WO | WO-2010/027259 A1 | 3/2010 | |
| WO | WO 2010027258 A1 * | 3/2010 | ............... A23L 1/30 |
| WO | WO-2010/068086 A1 | 6/2010 | |
| WO | WO-2010/068103 A1 | 6/2010 | |
| WO | WO-2010/068105 A1 | 6/2010 | |
| WO | WO-2011/108934 A1 | 9/2011 | |

OTHER PUBLICATIONS

Database WPI Week 200937, Thompson Scientific, London, GB, AN 2009-J69887, May 28, 2009, XP002578379.
Hamilton, "Interactions of Triglycerides with Phospholipids; Incorporation into the Bilayer Structure and Formation of Emulsions," 28, Biochem, 2514-2520 (1989).
Hur et al., "Influence of initial emulsifier type on microstructural changes occurring in emulsified lipids during in vitro digestion," Food Chemistry, vol. 114, pp. 253-262, XP002607759 (2009).
International Preliminary Report on Patentability for PCT/NL2011/050156—mailed Aug. 24, 2012.
International Preliminary Report on Patentability for PCT/NL2011/050188—mailed Jun. 15, 2012.
International Preliminary Report on Patentability mailed Jul. 19, 2010 in PCT/NL2009/050343.
International Search Report for PCT/NL2009/050525, mailed Dec. 1, 2009 (3 pages).
International Search Report for PCT/NL2011/050156—mailed Jun. 1, 2011.
International Search Report for PCT/NL2011/050188—mailed Jul. 5, 2011.
International Search Report in Application No. PCT/NL2009/050756 dated May 11, 2010.
International Search Report in Application PCT/NL2009/050754 dated May 7, 2010.
International Search Report mailed Dec. 14, 2009 in Application No. PCT/NL2009/050526.
International Search Report mailed Jul. 15, 2009 in PCT/NL2009/050343.
Joscelyne et al., "Food Emulsions Using Membrane Emulsification; Conditions for Producing Small Droplets," vol. 39, Journal of Food Engineering, pp. 59-64(1999).
Michalski et al., "Optical parameters of milk fat globules for laser light scattering measurements," Lait, 81(6):787-796 (2001).
Michalski et al., "The Dispersion State of Milk Fat Influences Triglyceride Metabolism in the Rat," European Journal of Nutrition, 44:436-444 (2005).
Michalski et al., "The Supramolecular Structure of Milk Fat Influences Plasma Triacylglycerols and Fatty Acid Profile in the Rat," European Journal of Nutrition, 45:215-224 (2006).
Mun et al., "Influence of interfacial composition on in vitro digestibility of emulsified lipids: potential mechanism for chitosan's ability to inhibit fat digestion," Food Biophysics, vol. 1, pp. 21-29, XP002607758 (2006).
Osteoporosis, PubMed Health, available at http;www.ncbi.nlm.nih.gov/pubmedhealth/PMH0001400, 2012.
Park et al., "Influence of encapsulation of emulsified lipids with chitosan on their in vivo digestibility," Food Chemistry, vol. 104, pp. 761-767, XP002607757 (2007).
Vickers, et al., "Supplementation with a Mixture of Complex Lipids Derived from Milk to Growing Rats Results in Improvements in Parameters Related to Growth and Cognition," Nutrition Research, 29:426-435 (2009).
Agostoni et al: "Polyunsaturated Fatty Acids in Human Milk and Neurological Development", Current Pediatric Reviews, vol. 1, 2005, pp. 25-30, XP002643794.
International Preliminary Report on Patentability for PCT/NL2011/050178—mailed Jun. 13, 2012.
International Search Report for PCT/NL2011/050187—mailed Jul. 5, 2011.
Jensen et al: "Specialty Lipids for Infant Nutrition. I. Milks and Formulas", Journal of Pediatric Gastroenterlogy and Nutrition, vol. 15, No. 3, 1992, pp. 232-245, XP002620897.
Makrides et al: "Fatty acid composition of brain, retina, and erythrocytes in breast- and formula-fed infants", American Journal of Clinical Nutrition, US, vol. 60, No. 2, 1994, pp. 189-194, XP002620896.
Michalski, et al: "Size Distribution of Fat Globules in Human Colostrum, Breast Milk, and Infant Formula", Journal of Dairy Science, American Dairy Science Association, vol. 88, Jan. 1, 2005, pp. 1927-1940, XP002505628.
Durand, A. et al. "Particle sizes and stability of UHT bovine, cereal and grain milks", Food Hydrocolloids, 2003, vol. 17, pp. 671-678.
Fave, G. et al. "Physicochemical properties of lipids; New strategies to manage fatty acid bioavailability", Cellular and Molecular Biology, 2004, vol. 50, No. 7, pp. 815-831.
McClements, D. "Food Emulsions—Principles, Practices, and Techniques", CRC Press, Second Edition, 2005, Section 7.3.
Michalski, M. et al. "Size Distribution of Fat Globules in Human Colostrum, Breast Milk, and Infant Formula", J. Dairy Sci., 2005, vol. 88, pp. 1927-1940.
Petrowski, G. "Emulson stability and its relation to foods", Emulsion Stability, 1976, pp. 309-359.
Ruegg, et al. "The Fat globule size distribution in human milk", Biochimica et Biophysica Acta, 1981, vol. 666., pp. 7-14.
Schultz, S. et al. "High-Pressure homogenization as a process for emulsion formation", Chem. Eng. Technol., 2004, vol. 27, No. 4, pp. 361-368.
Simonin, C. et al. "Comparison of the fat content and fat globule size distribution of breast milk from mothers delivering term and preterm", The American Journal of Clinical Nutrition, Oct. 1984, vol. 40, pp. 820-826.
Whittlestone, W. et al. "Variations in the Fat Content of Human Milk During Suckling", Ruakura Animal Research Station, Department of Agriculture, pp. 204-206, Jun. 1954.
Holman et al: "Deficiency of essential fatty acids and membrane fluidity during pregnancy and lactation", Proceedings of the National Acacemy of Sciences of the United States of America, vol. 88, No. 11, Jun. 1, 1991, pp. 4835-4839, XP002620898.
Marmot, et al. "Effect of breast-feeding on plasma cholesterol and weight in young adults", Journal of Epidemiology and Community Health (1980), vol. 34, pp. 164-167.
Owen, et al. "Infant Feeding and Blood Cholesterol: A Study in Adolescents and a Systematic Review", Pediatrics (2006) vol. 110, pp. 597-608.

* cited by examiner

INFANT NUTRITION FOR IMPROVING FATTY ACID COMPOSITION OF BRAIN MEMBRANES

FIELD OF THE INVENTION

The present invention relates to nutrition comprising special lipid globules, in particular to infant nutrition, for improvement of the fatty acid composition in brain membranes.

BACKGROUND OF THE INVENTION

Breast-feeding is the preferred method of feeding infants. However, there are circumstances that make breast-feeding impossible or less desirable. In those cases infant formulae are a good alternative. The composition of modern infant formulae is adapted in such a way that it meets many of the special nutritional requirements of the fast growing and developing infant.

Still it seems that improvements can be made towards the constitution of infant milk formulae. Early nutrition administered during the specific period of infancy when rapid growth and development of the body occurs has an imprinting or programming effect and therefore has long term metabolic consequences. Breast fed infants have a decreased chance of becoming obese later in life. Breast-fed infants score better on visual and developmental tests than do formula-fed infants and have an improved neurodevelopment compared to formula fed infants. Also long term links have been reported between breast milk feeding and cognitive ability or neurological status later in life.

This difference in neurodevelopment between breast and bottle fed infants has mainly been attributed to the presence of long chain polyunsaturated fatty acids (LC-PUFA) such as docosahexaenoic acid (DHA) and arachidonic acid (ARA) in breast milk. Most current infant milk formulae therefore now also comprise such LC-PUFA. It has also been found that such LC-PUFA are better incorporated into membranes when they are present in the diet in the form of phospholipids instead of triglycerides.

WO 2008/005033 discloses infant formula comprising fat, protein, carbohydrate, vitamins, and minerals, including gangliosides, phospholipids, (lipid-bound) sialic acid, docosahexaenoic acid, and arachidonic acid for early brain development such as accelarating neural migration.

WO 2005/051091 discloses a specific blend of glycerophospholipids in combination with sphingomyelin and/or cholesterol, which blend resembles that of human breast milk and is present as a fat globule for use in the manufacture of infant formulae. The blend is claimed to be beneficial for the development of cognitive and vision functions of the fetus, infants and children.

WO 2009/057121 discloses a method for improving, promoting or maintaining the development of brain and retina in an infant comprising administering a composition comprising at least one triglyceride, at least one phospholipid and at least one long chain poly-unsaturated fatty acid (LC-PUFA); wherein at least about 1% of the LC-PUFA in the composition is conjugated to said at least one phospholipid.

WO 2009/051502 discloses the use of one or more complex lipids including gangliosides to achieve particular health benefits including maintaining or increasing cognitive development or maintaining or increasing growth in a foetal, infant or child subject.

US 2008-292724 discloses that upon administration of a composition that comprises: a) a lipid fraction comprising at least one of docosahexaenoic acid (DHA), docosapentaenoic acid (DPA) and eicosapentaenoic acid (EPA); b) a protein fraction comprising proteinaceous material from non-human origin which provide at least cysteine and/or taurine; and c) a mineral fraction comprising at least one of manganese and molybdene, the health of these persons improves. Membrane function of cells improves, which allows efficient treatment of disorders, amongst which cognitive dysfunction and other diseases of the nervous system, neuropathies WO 2009/138680 discloses that the presence of at least 30% milk fat in conjunction with a vegetable oil in infant nutrition can be used amongst others to increase DHA accumulation in brain membranes, and ameloriating brain development and cognitive function. Optionally milk phospholipids are present.

WO 2008/081934 discloses an agent for facilitating the development of the brain in an infant, which comprises an effective amount of a milk-derived phospholipid or a sphingomyelin.

WO 2007/073193 discloses that in IMF with low levels of n6 PUFA, necessary to prevent obesity later in life, the incorporation of the small amount of n6 (LC-)PUFA into neurological cell membranes is more efficient by providing lipidic membrane components such as cholesterol, phospholipids and/or sphingolipids.

Benoit et al, 2010, Food Chem, 120:684-691, disclose that PC is an efficient carrier for DHA accretion in membranes and that in this respect also the specific structurisation of most PL in human milk, in the native milk fat globule membrane, which cannot be copied in infant formula, may be of functional significance for the infant.

Vickers et al, 2009, Nutr. Res., 29:426-435, disclose that high levels of complex lipids derived from milk improved parameters related to cognition. The amount of phospholipids based on total fat intake exceeded 6 wt. %, the phospholipids were administered separately via gavage, and also docosahexaenoic was supplemented to the complex lipid supplement.

SUMMARY OF THE INVENTION

Using rodent animal models the inventors found that even after a long period during which all the animals were on the same Western style diet, the effects of a previous early diet administered during infancy were still present with regard to the fatty acid profile of the brain membranes. Since fatty acid accretion of the brain and turnover in the brain is a continuous process throughout life, it was unexpected that such long term early diets effects were observed. The most surprising finding however, was that this effect was observed with infancy diets with a similar fat composition, only differing in the architecture of the dietary lipid globules. Effects on long term brain membrane fatty acid composition were observed regarding the presence and location of phospholipids and the size of the lipid globules. Phospholipids were most effective when located in the coating, i.e. outer layer, of the lipid globule, instead of being present as a free ingredient. Best results were obtained with an early diet comprising large lipid globules coated with phospholipids resulting in a long term increased percentage of PUFA and LC-PUFA in brain membranes, in particular DHA, indicative for increased membrane fluidity. Preferably, the lipid globules have to be both surrounded by a coating comprising phospholipids and increased in size in order to see improved long term effect on brain fatty acid composition compared to lipid globules as present in standard IMF.

This effect was consistently found in several independent experiments. In other animal experiments a direct effect of size and coating of lipid globules on brain membrane fatty acids was observed, even after 5 days of feeding in a young animal. Increased membrane fluidity, LC-PUFA content and n3/n6 PUFA ratio in brain membranes are known to be correlated to improve cognitive and behavioral performance. Hence the present invention can be used to improve these performances or to treat and/or prevent cognitive or behavioral disorders.

Cognitive improvement was indeed demonstrated in animals having administered the composition of the present invention, as demonstrated by a short version of the Morris water maze test.

The present invention therefore relates to nutrition, in particular infant nutrition, comprising lipid in the form of lipid globules, coated with polar lipids including phospholipids, and that are preferably large in size, for use in the development of cognitive or behavioural performances, including fine motor skills and visual acuity.

DETAILED DESCRIPTION

The present invention thus concerns a method for i) increasing brain membrane fluidity, ii) increasing brain membrane PUFA, iii) increasing brain membrane LC-PUFA, iv) decreasing ratio of brain membrane n6/n3 LC-PUFA, v) decreasing ratio of brain membrane n6/n3 PUFA, vi) increasing brain membrane n3 PUFA, vii) increasing brain membrane n3 LC-PUFA and/or viii) increasing brain membrane DHA, in a human subject, by administration of a nutritional composition comprising
a) 10 to 50 wt. % vegetable lipids based on dry weight of the composition, and
b1) 0.5 to 20 wt. % phospholipids based on total lipid and/or
b2) 0.6 to 25 wt. % of polar lipids based on total lipids, wherein polar lipids are the sum of phospholipids, glycosphingolipids and cholesterol,
and said composition comprising lipid globules with a core comprising said vegetable lipids and a coating comprising said phospholipids or polar lipids.

In one aspect present invention concerns a method for altering brain membrane fatty acid composition.

In one embodiment the present invention concerns a method for altering brain membrane fatty acid composition selected from the group consisting of i) increasing brain membrane fluidity, ii) increasing brain membrane PUFA, iii) increasing brain membrane LC-PUFA, iv) decreasing ratio of brain membrane n6/n3 LC-PUFA, v) decreasing ratio of brain membrane n6/n3 PUFA, vi) increasing brain membrane n3 PUFA, vii) increasing brain membrane n3 LC-PUFA and viii) increasing brain membrane DHA, in a human subject, by administration of a nutritional composition comprising
a) 10 to 50 wt. % vegetable lipids based on dry weight of the composition, and
b1) 0.5 to 20 wt. % phospholipids based on total lipid and/or
b2) 0.6 to 25 wt. % of polar lipids based on total lipids, wherein polar lipids are the sum of phospholipids, glycosphingolipids and cholesterol,
and said composition comprising lipid globules with a core comprising said vegetable lipids and a coating comprising said phospholipids or polar lipids.

In one embodiment the present method is non-therapeutic.

The present invention can also be worded as the use of a composition comprising lipid, or the use of lipid, for the manufacture of a nutritional composition for altering brain membrane fatty acid composition selected from the group consisting of i) increasing brain membrane fluidity, ii) increasing brain membrane PUFA, iii) increasing brain membrane LC-PUFA, iv) decreasing ratio of brain membrane n6/n3 LC-PUFA, v) decreasing ratio of brain membrane n6/n3 PUFA, vi) increasing brain membrane n3 PUFA, vii) increasing brain membrane n3 LC-PUFA and viii) increasing brain membrane DHA, in a human subject, said nutritional composition comprising
a) 10 to 50 wt. % vegetable lipids based on dry weight of the composition, and
b1) 0.5 to 20 wt. % phospholipids based on total lipid and/or
b2) 0.6 to 25 wt. % of polar lipids based on total lipids, wherein polar lipids are the sum of phospholipids, glycosphingolipids and cholesterol,
and said composition comprising lipid globules with a core comprising said vegetable lipids and a coating comprising said phospholipids or polar lipids.

The present invention can also be worded as a nutritional composition comprising
a) 10 to 50 wt. % vegetable lipids based on dry weight of the composition, and
b1) 0.5 to 20 wt. % phospholipids based on total lipid and/or
b2) 0.6 to 25 wt. % of polar lipids based on total lipids, wherein polar lipids are the sum of phospholipids, glycosphingolipids and cholesterol,
and said composition comprising lipid globules with a core comprising said vegetable lipids and a coating comprising said phospholipids or polar lipids
for use in altering brain membrane fatty acid composition selected from the group consisting of i) increasing brain membrane fluidity, ii) increasing brain membrane PUFA, iii) increasing brain membrane LC-PUFA, iv) decreasing ratio of brain membrane n6/n3 LC-PUFA, v) decreasing ratio of brain membrane n6/n3 PUFA, vi) increasing brain membrane n3 PUFA, vii) increasing brain membrane n3 LC-PUFA and viii) increasing brain membrane DHA, in a human subject.

In one embodiment the present invention is for the prevention and/or treatment of a disorder associated with decreased brain membrane fluidity and/or associated with decreased brain membrane PUFA content and/or LC-PUFA content. In one embodiment, the disorder is a psychiatric, psychological and/or neurobiological disorder. In one embodiment the present invention is for amelioration of i) cognitive performance, preferably memory performance and/or language development performance, more preferably learning memory performance, ii) behavioural performance, iii) visual acuity, iv) fine motor skills.

In one aspect the invention concerns a method for the prevention and/or treatment of a disorder associated with decreased brain membrane fluidity and/or associated with decreased brain membrane PUFA content and/or LC-PUFA content and/or increased ratio of n6/n3 LC-PUFA, and/or increased ratio of n6/n3 PUFA by administration to a human subject of a nutritional comprising
a) 10 to 50 wt. % vegetable lipids based on dry weight of the composition, and
b1) 0.5 to 20 wt. % phospholipids based on total lipid and/or
b2) 0.6 to 25 wt. % of polar lipids based on total lipids, wherein polar lipids are the sum of phospholipids, glycosphingolipids and cholesterol, and said composition comprising lipid globules with a core comprising said vegetable lipids and a coating comprising said phospholipids or polar lipids.

In one aspect, the present invention thus concerns a method for treatment and/or prevention of a disorder selected from the group consisting of attention deficiency, ADHD, dyslexia, autism, depression, bipolar depression, anxiety, schizophrenia, obsessive-compulsive disorder (OCD), bulimia, abuse of alcohol or drugs, borderline personality disorder, panic disorder, social phobia, learning difficulties, mild cognitive impairment, learning memory impairment, language development impairment, dementia, Alzheimer's disease and Parkinson's disease, said method comprising administering to a human subject a nutritional composition comprising
a) 10 to 50 wt. % vegetable lipids based on dry weight of the composition, and
b1) 0.5 to 20 wt. % phospholipids based on total lipid and/or
b2) 0.6 to 25 wt. % of polar lipids based on total lipids, wherein polar lipids are the sum of phospholipids, glycosphingolipids and cholesterol,
and said composition comprising lipid globules with a core comprising said vegetable lipids and a coating comprising said phospholipids or polar lipids The present invention can also be worded as the use of a composition comprising lipid, or the use of lipid, for the manufacture of a nutritional composition for treatment and/or prevention of a disorder selected from the group consisting of attention deficiency, ADHD, dyslexia, autism, depression, bipolar depression, anxiety, schizophrenia, OCD, bulimia, abuse of alcohol or drugs, borderline personality disorder, panic disorder, social phobia, learning difficulties, mild cognitive impairment learning memory impairment, language development impairment, dementia, Alzheimer's disease and Parkinson's disease in a human subject, said nutritional composition comprising
a) 10 to 50 wt. % vegetable lipids based on dry weight of the composition, and
b1) 0.5 to 20 wt. % phospholipids based on total lipid and/or
b2) 0.6 to 25 wt. % of polar lipids based on total lipids, wherein polar lipids are the sum of phospholipids, glycosphingolipids and cholesterol,
and said composition comprising lipid globules with a core comprising said vegetable lipids and a coating comprising said phospholipids or polar lipids.

The present invention can also be worded as a nutritional composition comprising
a) 10 to 50 wt. % vegetable lipids based on dry weight of the composition, and
b1) 0.5 to 20 wt. % phospholipids based on total lipid and/or
b2) 0.6 to 25 wt. % of polar lipids based on total lipids, wherein polar lipids are the sum of phospholipids, glycosphingolipids and cholesterol,
and said composition comprising lipid globules with a core comprising said vegetable lipids and a coating comprising said phospholipids or polar lipids
for use in treatment and/or prevention of a disorder selected from the group consisting of attention deficiency, ADHD, dyslexia, autism, depression, bipolar depression, anxiety, schizophrenia, OCD, bulimia, abuse of alcohol or drugs, borderline personality disorder, panic disorder, social phobia, learning difficulties, mild cognitive impairment learning memory impairment, language development impairment, dementia, Alzheimer's disease and Parkinson's disease in a human subject.

In one aspect, the present invention concerns a method for amelioration of i) cognitive performance, preferably memory performance and/or language development performance, more preferably learning memory performance, ii) behavioural performance, iii) visual acuity, iv) fine motor skills, in a human subject, said method comprising administering to a human subject, or in other words by administration to a human subject of, a nutritional composition comprising
a) 10 to 50 wt. % vegetable lipids based on dry weight of the composition, and
b1) 0.5 to 20 wt. % phospholipids based on total lipid and/or
b2) 0.6 to 25 wt. % of polar lipids based on total lipids, wherein polar lipids are the sum of phospholipids, glycosphingolipids and cholesterol,
and said composition comprising lipid globules with a core comprising said vegetable lipids and a coating comprising said phospholipids or polar lipids.

In one embodiment of this aspect, the method is non-therapeutic.

The invention can also be worded as the use of a composition comprising lipid, or the use of lipid, for the manufacture of a nutritional composition for amelioration of i) cognitive performance, preferably memory performance and/or language development performance, more preferably learning memory performance, ii) behavioural performance, iii) visual acuity, iv) fine motor skills in a human subject, said nutritional composition comprising
a) 10 to 50 wt. % vegetable lipids based on dry weight of the composition, and
b1) 0.5 to 20 wt. % phospholipids based on total lipid and/or
b2) 0.6 to 25 wt. % of polar lipids based on total lipids, wherein polar lipids are the sum of phospholipids, glycosphingolipids and cholesterol,
and said composition comprising lipid globules with a core comprising said vegetable lipids and a coating comprising said phospholipids or polar lipids.

The present invention can also be worded as a nutritional composition comprising
a) 10 to 50 wt. % vegetable lipids based on dry weight of the composition, and
b1) 0.5 to 20 wt. % phospholipids based on total lipid and/or
b2) 0.6 to 25 wt. % of polar lipids based on total lipids, wherein polar lipids are the sum of phospholipids, glycosphingolipids and cholesterol,
and said composition comprising lipid globules with a core comprising said vegetable lipids and a coating comprising said phospholipids or polar lipids
for use in amelioration of i) cognitive performance, preferably memory performance and/or language development performance, more preferably learning memory performance, ii) behavioural performance, iii) visual acuity, iv) fine motor skills in a human subject.

For sake of clarity it is noted that the present invention is defined in terms of specific ingredients, hence the vegetable lipids and phospholipids and polar lipids and by the way these ingredients are assembled, hence as phospholipid or polar lipid coated lipid globules of a certain size. Hence the ingredients and the way they are assembled overlap.

Throughout the description wherever the phrase 'the present composition' is used it is to be understood that this refers to the composition that is used in the method according to the present invention or in other words for the use to achieve the specified effect(s).

Lipid Component

The present composition comprises lipid. The lipid provides preferably 30 to 60% of the total calories of the composition. More preferably the present composition comprises lipid providing 35 to 55% of the total calories, even more preferably the present composition comprises lipid providing 40 to 50% of the total calories. When in liquid form, e.g. as a ready-to-feed liquid, the composition preferably comprises 2.1 to 6.5 g lipid per 100 ml, more preferably 3.0 to 4.0 g per 100 ml. Based on dry weight the present composition preferably comprises 10 to 50 wt. %, more preferably 12.5 to 40 wt. % lipid, even more preferably 19 to 30 wt. % lipid.

Lipids include polar lipids (such as phospholipids, glycolipids, sphingomyelin, and cholesterol), monoglycerides, diglycerides, triglycerides and free fatty acids. Preferably the composition comprises at least 75 wt. %, more preferably at least 85 wt. % triglycerides based on total lipids.

The lipid of the present invention comprises vegetable lipids. The presence of vegetable lipids advantageously enables an optimal fatty acid profile, high in (poly)unsaturated fatty acids and/or more reminiscent to human milk fat. Using lipids from cow's milk alone, or other domestic mammals, does not provide an optimal fatty acid profile. Preferably the present composition comprises at least one, preferably at least two lipid sources selected from the group consisting of linseed oil (flaxseed oil), rape seed oil (such as colza oil, low erucic acid rape seed oil and canola oil), salvia oil, perilla oil, purslane oil, lingonberry oil, sea buckthorn oil, hemp oil, sunflower oil, high oleic sunflower oil, safflower oil, high oleic safflower oil, olive oil, black currant seed oil, echium oil, coconut oil, palm oil and palm kernel oil. Preferably the present composition comprises at least one, preferably at least two lipid sources selected from the group consisting of linseed oil, canola oil, coconut oil, sunflower oil and high oleic sunflower oil. Commercially available vegetable lipids are typically offered in the form a continuous oil phase. When in liquid form, e.g. as a ready-to-feed liquid, the composition preferably comprises 2.1 to 6.5 g vegetable lipid per 100 ml, more preferably 3.0 to 4.0 g per 100 ml. Based on dry weight the present composition preferably comprises 10 to 50 wt. %, more preferably 12.5 to 40 wt. % vegetable lipid, even more preferably 19 to 30 wt. %. Preferably the composition comprises 50 to 100 wt. % vegetable lipids based on total lipids, more preferably 70 to 100 wt. %, even more preferably 75 to 97 wt. %. It is noted therefore that the present composition also may comprise non-vegetable lipids. Suitable and preferred non-vegetable lipids are further specified below.

Polar Lipids

The present invention comprises polar lipids. Polar lipids are amphipathic of nature and include glycerophospholipids, glycosphingolipids, sphingomyelin and/or cholesterol. More preferably the composition comprises phospholipids (the sum of glycerophospholipids and sphingomyelin). Polar lipids in the present invention relate to the sum of glycerophospholipids, glycosphingolipids, sphingomyelin and cholesterol. According to the present invention polar lipids are present as a coating of the lipid globule. By 'coating' is meant that the outer surface layer of the lipid globule comprises polar lipids, whereas these polar lipids are virtually absent in the core of the lipid globule. The presence of polar lipids as a coating or outer layer of the lipid globule in the diet administered early in life was found to advantageously result in increased incorporation of (LC-)PUFA in brain cell membranes later in life.

The present composition preferably comprises glycerophospholipids. Glycerophospholipids are a class of lipids formed from fatty acids esterified at the hydroxyl groups on carbon-1 and carbon-2 of the backbone glycerol moiety and a negatively-charged phosphate group attached to carbon-3 of the glycerol via an ester bond, and optionally a choline group (in case of phosphatidylcholine, PC), a serine group (in case of phosphatidylserine, PS), an ethanolamine group (in case of phosphatidylethanolamine, PE), an inositol group (in case of phosphatidylinositol, PI) or a glycerol group (in case of phosphatidylglycerol, PG) attached to the phosphate group. Lysophospholipids are a class of phospholipids with one fatty acyl chain. Preferably the present composition contains PC, PS, PI and/or PE, more preferably at least PC.

The present composition preferably comprises phosphospingolipids, preferably sphingomyelin. Sphingomyelins have a phosphorylcholine or phosphorylethanolamine molecule esterified to the 1-hydroxy group of a ceramide. They are classified as phospholipid as well as sphingolipid, but are not classified as a glycerophospholipid nor as a glycosphingolipid.

The present composition preferably comprises glycosphingolipids. The term glycosphingolipids as in the present invention particularly refers to glycolipids with an amino alcohol sphingosine. The sphingosine backbone is O-linked to a charged headgroup such as ethanolamine, serine or choline backbone. The backbone is also amide linked to a fatty acyl group. Glycosphingolipids are ceramides with one or more sugar residues joined in a β-glycosidic linkage at the 1-hydroxyl position. Preferably the present composition contains gangliosides, more preferably at least one ganglioside selected from the group consisting of GM3 and GD3.

Sphingolipids are in the present invention defined as the sum of sphingomyelin and glycosphingolipids. Phospholipids are in the present invention defined as the sum of sphingomyelin and glycerophospholipids. Preferably the phospholipids are derived from milk lipids. Preferably the weight ratio of phospholipids:glycosphingolipids is from 2:1 to 10:1, more preferably 2:1 to 5:1.

Preferably the present composition comprises phospholipids. Preferably the present composition comprises 0.5 to 20 wt. % phospholipids based on total lipid, more preferably 0.5 to 10 wt. %, more preferably 1 to 10 wt. %, even more preferably 1 to 5 wt. %, even more preferably 2 to 10 wt. % even more preferably 2 to 5 wt. %, even more preferably 0.5 to 5 wt. % and even more preferably 1 to 3 wt. % phospholipids based on total lipid. Preferably the present composition comprises 0.1 to 10 wt. % glycosphingolipids based on total lipid, more preferably 0.5 to 5 wt. %, even more preferably 2 to 4 wt %. Preferably the present composition comprises 0.5 to 10 wt. % (glycosphingolipids plus phospholipids) based on total lipid, more preferably 1.0 to 10 wt. % (glycosphingolipids plus phospholipids), more preferably 0.5 to 6 wt. % (glycosphingolipids plus phospholipids), more preferably 0.5 to 3.5 wt. % (glycosphingolipids plus phospholipids), more preferably 1.0 to 6 wt. % (glycosphingolipids plus phospholipids), more preferably 1.0 to 3.5 wt. % (glycosphingolipids plus phospholipids) based on total lipid.

The present composition preferably comprises cholesterol. The present composition preferably comprises at least 0.005 wt. % cholesterol based on total lipid, more preferably at least 0.02 wt. %, more preferably at least 0.05 wt. %, even more preferably at least 0.1 wt. %. Preferably the amount of cholesterol does not exceed 10 wt. % based on total lipid, more preferably does not exceed 5 wt. %, even more preferably does not exceed 1 wt. % of total lipid.

Preferably the present composition comprises 0.6 to 25 wt. % polar lipids based on total lipid, wherein the polar lipids are the sum of phospholipids, glycosphingolipids, and cholesterol, more preferably 0.6 to 12 wt. %, more preferably 0.6 to 6 wt. %, more preferably 1 to 10 wt. %, even more preferably 2 to 10 wt %, even more preferably 3.0 to 10 wt. % polar lipids based on total lipid, wherein the polar lipids are the sum of phospholipids, glycosphingolipids, and cholesterol.

Preferred sources for providing the phospholipids, glycosphingolipids and/or cholesterol are egg lipids, milk fat, buttermilk fat and butter serum fat (such as beta serum fat). A preferred source for phospholipids, particularly PC, is soy lecithin and/or sunflower lecithin. The present composition preferably comprises phospholipids derived from milk. Preferably the present composition comprises phospholipids and glycosphingolipids derived from milk. Preferably also cholesterol is obtained from milk. Preferably the polar lipids are derived from milk. Polar lipids derived from milk include the polar lipids isolated from milk lipid, cream lipid, butter serum lipid (beta serum lipid), whey lipid, cheese lipid and/or buttermilk lipid. The buttermilk lipid is typically obtained during the manufacture of buttermilk. The butter serum lipid or beta serum lipid is typically obtained during the manufacture of anhydrous milk fat from butter. Preferably the phospholipids, glycosphingolipids and/or cholesterol are obtained from milk cream. The composition preferably comprises phospholipids, glycosphingolipids and/or cholesterol from milk of cows, mares, sheep, goats, buffalos, horses and camels. It is most preferred to use a lipid extract isolated from cow's milk. The use of polar lipids from milk fat advantageously comprises the polar lipids from milk fat globule membranes, which are more reminiscent to the situation in human milk. Polar lipids derived from fat milk advantageously improve brain fatty acid composition to a larger extent than polar lipids from other sources. The polar lipids are located on the surface of the lipid globule, i.e. as a coating or outer layer. A suitable way to determine whether the polar lipids are located on the surface of the lipid globules is laser scanning microscopy as given in example 1. The concomitant use of polar lipids derived from domestic animals milk and triglycerides derived from vegetable lipids therefore enables to manufacture coated lipid globules with a coating more similar to human milk, while at the same time providing an optimal fatty acid profile. Suitable commercially available sources for milk polar lipids are BAEF, SM2, SM3 and SM4 powder of Corman, Salibra of Glanbia, and LacProdan MFGM-10 or PL20 from Arla. Preferably the source of milk polar lipids comprises at least 4 wt. % phospholipids based on total lipid, more preferably 7 to 75 wt. %, most preferably 20 to 70 wt. % phospholipids based on total lipid. Preferably the weight ratio phospholipids to protein is above 0.10, more preferably above 0.20, even more preferably above 0.3. Preferably at least 25 wt. %, more preferably at least 40 wt. %, most preferably at least 75 wt. % of the polar lipids is derived from milk polar lipids.

Fatty Acid Composition

Herein LA refers to linoleic acid and/or acyl chain (18:2 n6); ALA refers to α-linolenic acid and/or acyl chain (18:3 n3); LC-PUFA refers to long chain polyunsaturated fatty acids and/or acyl chains comprising at least 20 carbon atoms in the fatty acyl chain and with 2 or more unsaturated bonds; DHA refers to docosahexaenoic acid and/or acyl chain (22:6, n3); EPA refers to eicosapentaenoic acid and/or acyl chain (20:5 n3); ARA refers to arachidonic acid and/or acyl chain (20:4 n6); DPA refers to docosapentaenoic acid and/or acyl chain (22:5 n3). Medium chain fatty acids (MCFA) refer to fatty acids and/or acyl chains with a chain length of 6, 8 or 10 carbon atoms.

LA preferably is present in a sufficient amount in order to promote a healthy growth and development, yet in an amount as low as possible in view of an unwanted high n6/n3 ratio. The composition therefore preferably comprises less than 15 wt. % LA based on total fatty acids, preferably between 5 and 14.5 wt. %, more preferably between 6 and 10 wt. %. Preferably the composition comprises over 5 wt. % LA based on fatty acids. Preferably ALA is present in a sufficient amount to promote a healthy growth and development of the infant. The present composition therefore preferably comprises at least 1.0 wt. % ALA based on total fatty acids. Preferably the composition comprises at least 1.5 wt. % ALA based on total fatty acids, more preferably at least 2.0 wt. %. Preferably the composition comprises less than 10 wt. % ALA, more preferably less than 5.0 wt. % based on total fatty acids. The weight ratio LA/ALA should be well balanced ensuring a normal growth and development. Therefore, the present composition preferably comprises a weight ratio of LA/ALA between 2 and 15, more preferably between 2 and 7, more preferably between 4 and 7, more preferably between 3 and 6, even more preferably between 4 and 5.5, even more preferably between 4 and 5.

The present composition preferably comprises at least 3 wt. % MCFA based on total fatty acids, more preferably at least 10 wt. %, even more preferably 15 wt. %. The present composition advantageously comprises less than 50 wt. % MCFA based on total fatty acids, more preferably less than 40 wt. %, even more preferably less than 25 wt. %.

Preferably the present composition comprises n3 LC-PUFA, since efficient incorporation of n3 LC-PUFA in brain membranes improve fluidity thereof. More preferably, the present composition comprises EPA, DPA and/or DHA, even more preferably DHA. Since a low concentration of DHA, DPA and/or EPA is already effective and normal growth and development are important, the content of n3 LC-PUFA in the present composition, preferably does not exceed 15 wt. % of the total fatty acid content, preferably does not exceed 10 wt. %, even more preferably does not exceed 5 wt. %. Preferably the present composition comprises at least 0.2 wt. %, preferably at least 0.5 wt. %, more preferably at least 0.75 wt. %, n3 LC-PUFA of the total fatty acid content. In one embodiment the present composition preferably comprises DHA in an amount of 0.1 to 0.6 wt. % based on total fatty acid content.

As the group of n6 fatty acids, especially arachidonic acid (ARA) and LA as its precursor, counteracts the group of n3 fatty acids, especially DHA and EPA and ALA as their precursor, the present composition comprises relatively low amounts of ARA. The n6 LC-PUFA content preferably does not exceed 5 wt. %, more preferably does not exceed 2.0 wt. %, more preferably does not exceed 0.75 wt. %, even more preferably does not exceed 0.5 wt. %, based on total fatty acids. Nevertheless, since according to the present invention incorporation into brain membranes is improved, still an advantageous effect on brain membrane fluidity can be obtained. Since ARA is important in infants for optimal functional membranes, especially membranes of brain tissues, the amount of n6 LC-PUFA is preferably at least 0.02 wt. % more preferably at least 0.05 wt. %, more preferably at least 0.1 wt. % based on total fatty acids, more preferably at least 0.2 wt. %. The presence of ARA is advantageous in a composition low in LA since it remedies LA deficiency. The presence of, preferably low amounts, of ARA is beneficial in nutrition to be administered to infants below the age of 6 months, since for these infants the infant formulae is generally the only source of nutrition. In one embodiment the present composition preferably comprises ARA in an amount of 0.1 to 0.6 wt. % based on total fatty acid content.

Preferably in addition to the vegetable lipid, a lipid selected from fish oil (preferably tuna fish oil) and single cell oil (such as algal, microbial oil and fungal oil) is present.

These sources of oil are suitable as LC-PUFA sources. Preferably as a source of n3 LC-PUFA single cell oil, including algal oil and microbial oil, is used, since these oil sources have an advantageous EPA/DHA ratio. More preferably fish oil (even more preferably tuna fish oil) is used as a source of n3 LC-PUFA since fish oil has a higher EPA concentration. Thus in one embodiment the present composition further comprises at least one lipid selected from the group consisting of fish oil, marine oil, algal oil, fungal oil and microbial oil.

Process for Obtaining Polar Lipid Coated Lipid Globules

The present composition comprises lipid globules. The lipid globule size can be manipulated by adjusting process steps by which the present composition is manufactured. A suitable and preferred way to obtain lipid globules coated with polar lipids is to increase the amount of polar lipids compared to amounts typically present in infant formula and to have these polar lipids present during the homogenization process, wherein the mixture of aqueous phase and oil phase is homogenized. Typical amounts of phospholipids/polar lipids in infant formula are about 0.15 wt. %/0.2 wt. % based on total fat. The amount of phospholipids is increased to at least 0.5 wt %, more preferably at least 1.0 wt. % based on total fat or the amount of polar lipids is increased to at least 0.6 wt. %, more preferably at least 1.0 wt. % based on total fat. In standard infant milk formula the lipid fraction (usually comprising vegetable fat, a small amount of polar lipids and fat soluble vitamins) is mixed into the aqueous fraction (usually comprising water, skimmed milk, whey, digestible carbohydrates such as lactose, water soluble vitamins and minerals and optionally non-digestible carbohydrates) by homogenization. If no homogenization was to take place, the lipid part would cream very quickly, i.e. separate from the aqueous part and collect at the top. Homogenization is the process of breaking up the fat phase into smaller sizes so that it no longer quickly separates from the aqueous phase but is maintained in a stable emulsion. This is accomplished by forcing the milk at high pressure through small orifices.

The process comprises the following steps:

1 Mixing Ingredients

The ingredients of the composition are mixed, e.g. preferably blended. Basically a lipid phase, comprising the vegetable lipids, and an aqueous phase are added together. The ingredients further comprise polar lipids, more preferably phospholipids. The ingredients of the aqueous phase may comprise water, skimmed milk (powder), whey (powder), low fat milk, lactose, water soluble vitamins and minerals. Preferably the aqueous phase comprises non-digestible oligosaccharides. Preferably the aqueous phase is set at a pH between 6.0 and 8.0, more preferably pH 6.5 to 7.5. Preferably the polar lipids, in particular the phospholipids, are derived from milk. Advantageously, having polar lipids present in the aqueous mixture before homogenization results in an efficient coating of the lipid globules, consisting essentially of triglycerides, with a coating of polar lipids.

Preferably the lipid phase comprises 50 to 100 wt. % vegetable lipids based on total weight of the lipid phase. Instead of in the aqueous phase, the polar lipids, more preferably the phospholipids, may also be present in the lipid phase or in both phases. Alternatively the polar lipids may be added separately to an aqueous and lipid phase. Preferably, the weight ratio of phospholipid to total lipid is from 0.5 to 20 wt. %, more preferably from 0.5 to 10 wt. %, even more preferably 3 to 8 wt. %. Preferably the weight ratio of polar lipids tot total lipid is 0.6 to 25 wt. %, more preferably from 0.6 to 12 wt. %

The aqueous and lipid phase are preferably heated before adding together, preferably at a temperature of 40° C. to 80° C., more preferably 55° C. to 70° C., even more preferably 55° C. to 60° C. The mixture is also kept at this temperature and blended. A suitable way for blending is using an Ultra-Turrax T50 for about 30-60 s at 5000-10000 rpm. Subsequently demi-water may be added to this blend, to obtain the desired dry matter %. A desired dry matter % is for example 15%. Alternatively, the lipid phase is injected to the aqueous phase immediately prior to homogenization.

Minerals, vitamins, and stabilizing gums may be added at various points in the process depending on their sensitivity to heat. Mixing can for instance be performed with a high shear agitator. In the process of the present invention, skimmed milk (casein) is preferably not present in this step and added to the composition after homogenization of the fat fraction into the aqueous fraction (comprising compounds such as whey, whey protein, lactose).

2 Pasteurization

Preferably the mixture is then pasteurized. Pasteurization involves a quick heating step under controlled conditions which microorganisms cannot survive. A temperature of 60 to 80° C., more preferably 65 to 75° C., held for at least 15 s, usually adequately reduces vegetative cells of microorganisms. Several pasteurization methods are known and commercially feasible. Alternatively this step can also be performed before mixing as in step 1 and/or be replaced by the heating step to 60° C. in step 1.

3 Homogenization

Subsequently the optionally pasteurized mixture comprising vegetable lipids, polar lipids and an aqueous phase is homogenized. Homogenization is a process which increases emulsion uniformity and stability by reducing the size of the lipid globules in the formula. This process step can be performed with a variety of mixing equipment, which applies high shear to the product. This type of mixing breaks the lipid globules into smaller globules. The mixture obtained is preferably homogenized in two steps, for example at 250 to 50 bar, respectively, so a total pressure of 300 bar in order to obtain small, stable lipid globules.

In case the size of the lipid globules is preferred to be larger the homogenization steps are performed under much lower pressures. For example 60° C. at 5 to 100, preferably 30-100, bar and 5 to 50 bar respectively, with a total pressure of 35 to 150 bar. Alternatively, the mixture obtained is preferably homogenized in two steps at a lower temperature, between 15 and 40° C., preferably about 20° C. at 5 to 50 and 5 to 50 bar respectively, with a total pressure of 5 to 100 bar. This is remarkably lower than standard pressures, which typically are 250 to 50 bar, respectively, so a total pressure of 300 bar. It will be dependent on the specific homogenizer used, which pressure to apply. A suitable way is to use a pressure of 100 bar in the first step and 50 bar in the second step in a Niro Suavi NS 2006 H Homogenizer at a temperature of 60° C. A suitable way is to use a pressure of 5 bar in the first step and 20 bar in the second step in a Niro Suavi NS 2006 H Homogenizer at a temperature of 20° C. Subsequently optionally other ingredients, not being lipid, may be added.

4 Sterilization

Subsequently, the emulsion obtained in step 3 is preferably sterilized. Preferably sterilization takes place in-line at ultra high temperature (UHT) and/or in appropriate containers to obtain a formula in the form of a sterile liquid. A suitable way for UHT treatment is a treatment at 120-130° C. for at least 20 s. Alternatively this sterilization step 4 is performed before the homogenization step 3.

Preferably the composition obtained by the above process is spray dried afterwards.

Alternatively, the emulsion obtained in step 3 is concentrated by evaporation, subsequently sterilized at ultra high temperature and subsequently spray dried to give a spray dried powder which is filled into appropriate containers.

The difference on coating of the lipid globules can further be derived from the zeta potential. Zeta potential (ζ potential) measures the difference in milliVolts (mV) in electrokinetic potential between the tightly bound layer around the surface and the distant zone of electroneutrality and is a measure of the magnitude of the repulsion or attraction between particles in a dispersion. Its value is also related to the stability of colloidal dispersions. A high absolute zeta potential will confer stability, i.e. the solution or dispersion will resist aggregation.

Lipid Globule Size

According to the present invention, lipid is present in the composition in the form of lipid globules, emulsified in the aqueous phase. The lipid globules comprise a core and a coating. The core comprises vegetable fat and preferably comprises at least 90 wt. % triglycerides and more preferably essentially consists of triglycerides. The coating comprises phospholipids and/or polar lipids. Not all phospholipids and/or polar lipids that are present in the composition need necessarily be comprised in the coating, but preferably a major part is. Preferably more than 50 wt. %, more preferably more than 70 wt, %, even more preferably more than 85 wt. %, most preferably more than 95 wt. % of the phospholipids and/or polar lipids that are present in the composition are comprised in the coating of lipid globules. Not all vegetable lipids that are present in the composition need necessarily be comprised in the core of lipid globules, but preferably a major part is, preferably more than 50% wt. %, more preferably more than 70 wt. %, even more preferably more than 85 wt. %, even more preferably more than 95 wt. %, most preferably more than 98 wt. % of the vegetable lipids that are present in the composition are comprised in the core of lipid globules.

In one embodiment the lipid globules of the present invention preferably have
1. a volume-weighted mode diameter above 1.0 μm, preferably above 3.0 μm, more preferably 4.0 μm or above, preferably between 1.0 and 10 μm, more preferably between 2.0 and 8.0 μm, even more preferably between 3.0 and 8.0 μm, most preferably between 4.0 μm and 8.0 μm and/or
2. a size distribution in such a way that at least 45 volume %, preferably at least 55 volume %, even more preferably at least 65 volume %, even more preferably at least 75 volume % has a diameter between 2 and 12 μm. More preferably at least 45 volume %, preferably at least 55 volume %, even more preferably at least 65 volume %, even more preferably at least 75 volume % has a diameter between 2 and 10 μm. Even more preferably at least 45 volume %, preferably at least 55 volume %, even more preferably at least 65 volume %, even more preferably at least 75 volume % has a diameter between 4 and 10 μm.

In another preferred embodiment the lipid globules of the present invention preferably have
1. a volume-weighted mode diameter below 1.0 μm, and preferably in the range of 0.2-0.7 μm, more preferably in the range of 0.3-0.6 μm, and
2. a size distribution in such a way that less than 45 volume %, has a diameter between 2 and 12 μm, preferably a size distribution wherein more than 55 volume % of the lipid globules has a diameter of less than 2 μm, more preferably a size distribution in such a way that less than 35 volume %, has a diameter between 2 and 12 μm, even more preferably a size distribution wherein more than 65 volume % of the lipid globules has a diameter of less than 2 μm.

The percentage of lipid globules is based on volume of total lipid. The mode diameter relates to the diameter which is the most present based on volume of total lipid, or the peak value in a graphic representation, having on the X-as the diameter and on the Y-as the volume (%).

The volume of the lipid globule and its size distribution can suitably be determined using a particle size analyzer such as a Mastersizer (Malvern Instruments, Malvern, UK), for example by the method described in Michalski et al, 2001, Lait 81: 787-796.

Digestible Carbohydrate Component

The composition preferably comprises digestible carbohydrate. The digestible carbohydrate preferably provides 30 to 80% of the total calories of the composition. Preferably the digestible carbohydrate provides 40 to 60% of the total calories. When in liquid form, e.g. as a ready-to-feed liquid, the composition preferably comprises 3.0 to 30 g digestible carbohydrate per 100 ml, more preferably 6.0 to 20, even more preferably 7.0 to 10.0 g per 100 ml. Based on dry weight the present composition preferably comprises 20 to 80 wt. %, more preferably 40 to 65 wt. % digestible carbohydrates.

Preferred digestible carbohydrate sources are lactose, glucose, sucrose, fructose, galactose, maltose, starch and maltodextrin. Lactose is the main digestible carbohydrate present in human milk. The present composition preferably comprises lactose. The present composition preferably comprises digestible carbohydrate, wherein at least 35 wt. %, more preferably at least 50 wt. %, more preferably at least 75 wt. %, even more preferably at least 90 wt. %, most preferably at least 95 wt. % of the digestible carbohydrate is lactose. Based on dry weight the present composition preferably comprises at least 25 wt. % lactose, preferably at least 40 wt. %.

Non-Digestible Oligosaccharides

Preferably the present composition comprises non-digestible oligosaccharides with a degree of polymerization (DP) between 2 and 250, more preferably 3 and 60. The non-digestible oligosaccharides advantageously improve intestinal microbiota.

The non-digestible oligosaccharide is preferably selected from the group consisting of fructo-oligosaccharides (such as inulin), galacto-oligosaccharides (such as transgalacto-oligosaccharides or beta-galacto-oligisaccharides), gluco-oligosaccharides (such as gentio-, nigero- and cyclodextrin-oligosaccharides), arabino-oligosaccharides, mannan-oligosaccharides, xylo-oligosaccharides, fuco-oligosaccharides, arabinogalacto-oligosaccharides, glucomanno-oligosaccharides, galactomanno-oligosaccharides, sialic acid comprising oligosaccharides and uronic acid oligosaccharides. Preferably the composition comprises gum acacia on combination with a non-digestible oligosaccharide.

Preferably the present composition comprises fructo-oligosaccharides, galacto-oligosaccharides and/or galacturonic acid oligosaccharides, more preferably galacto-oligosaccharides, most preferably transgalacto-oligosaccharides. In a preferred embodiment the composition comprises a mixture of transgalacto-oligosaccharides and fructo-oligosaccharides. Preferably the present composition comprises galacto-oligosaccharides with a DP of 2-10 and/or fructo-oligosaccharides with a DP of 2-60. The galacto-oligosaccharide is preferably selected from the group consisting of transgalacto-oligosaccharides, lacto-N-tetraose (LNT), lacto-N- neotetraose (neo-LNT), fucosyl-lactose, fucosylated LNT and fucosylated neo-LNT. In a particularly preferred embodiment the present method comprises the administration of transgalacto-oligosaccharides ([galactose]$_n$-glucose; wherein n is an integer between 1 and 60, i.e. 2, 3, 4, 5, 6, . . . , 59, 60; preferably n is selected from 2, 3, 4, 5, 6, 7, 8, 9, or 10). Transgalacto-oligosaccharides (TOS) are for example sold under the trademark Vivinal™ (Borculo Domo Ingredients, Netherlands). Preferably the saccharides of the transgalacto-oligosaccharides are β-linked.

Fructo-oligosaccharide is a non-digestible oligosaccharide comprising a chain of β linked fructose units with a DP or average DP of 2 to 250, more preferably 10 to 100. Fructo-oligosaccharide includes inulin, levan and/or a mixed type of polyfructan. An especially preferred fructo-oligosaccharide is inulin. Fructo-oligosaccharide suitable for use in the compositions is also already commercially available, e.g. Raftiline®HP (Orafti).

Uronic acid oligosaccharides are preferably obtained from pectin degradation. Uronic acid oligosaccharides are preferably galacturonic acid oligosaccharides. Hence the present composition preferably comprises a pectin degradation product with a DP between 2 and 100. Preferably the pectin degradation product is prepared from apple pectin, beet pectin and/or citrus pectin. Preferably the composition comprises transgalacto-oligosaccharide, fructo-oligosaccharide and a pectin degradation product. The weight ratio transgalacto-oligosaccharide:fructo-oligosaccharide:pectin degradation product is preferably (20 to 2):1:(1 to 3), more preferably (12 to 7):1:(1 to 2).

Preferably, the composition comprises of 80 mg to 2 g non-digestible oligosaccharides per 100 ml, more preferably 150 mg to 1.50 g, even more preferably 300 mg to 1 g per 100 ml. Based on dry weight, the composition preferably comprises 0.25 wt. % to 20 wt. %, more preferably 0.5 wt. % to 10 wt. %, even more preferably 1.5 wt. % to 7.5 wt. %. A lower amount of non-digestible oligosaccharides will be less effective in providing a beneficial prebiotic effect, whereas a too high amount will result in side-effects of bloating and abdominal discomfort.

Protein Component

The present composition preferably comprises proteins. The protein component preferably provides 5 to 15% of the total calories. Preferably the present composition comprises a protein component that provides 6 to 12% of the total calories. More preferably protein is present in the composition below 9% based on calories, more preferably the composition comprises between 7.2 and 8.0% protein based on total calories, even more preferably between 7.3 and 7.7% based on total calories. The protein concentration in a nutritional composition is determined by the sum of protein, peptides and free amino acids. Based on dry weight the composition preferably comprises less than 12 wt. % protein, more preferably between 9.6 to 12 wt. %, even more preferably 10 to 11 wt. %. Based on a ready-to-drink liquid product the composition preferably comprises less than 1.5 g protein per 100 ml, more preferably between 1.2 and 1.5 g, even more preferably between 1.25 and 1.35 g.

The source of the protein should be selected in such a way that the minimum requirements for essential amino acid content are met and satisfactory growth is ensured. Hence protein sources based on cows' milk proteins such as whey, casein and mixtures thereof and proteins based on soy, potato or pea are preferred. In case whey proteins are used, the protein source is preferably based on acid whey or sweet whey, whey protein isolate or mixtures thereof and may include α-lactalbumin and β-lactoglobulin. More preferably, the protein source is based on acid whey or sweet whey from which caseino-glyco-macropeptide (CGMP) has been removed. Removal of CGMP from sweet whey protein advantageously reduces the threonine content of the sweet whey protein. A reduced threonine content is also advantageously achieved by using acid whey. Optionally the protein source may be supplemented with free amino acids, such as methionine, histidine, tyrosine, arginine and/or tryptophan in order to improve the amino acid profile. Preferably α-lactalbumin enriched whey protein is used in order to optimize the amino acid profile. Using protein sources with an optimized amino acid profile closer to that of human breast milk enables all essential amino acids to be provided at reduced protein concentration, below 9% based on calories, preferably between 7.2 and 8.0% based on calories and still ensure a satisfactory growth. If sweet whey from which CGMP has been removed is used as the protein source, it is preferably supplemented by free arginine in an amount of from 0.1 to 3 wt. % and/or free histidine in an amount of from 0.1 to 1.5 wt. % based on total protein.

Preferably the composition comprises at least 3 wt. % casein based on dry weight. Preferably the casein is intact and/or non-hydrolyzed.

Nutritional Composition

The present composition is preferably particularly suitable for providing the daily nutritional requirements to a human with an age below 36 months, particularly an infant with the age below 24 months, even more preferably an infant with the age below 18 months, most preferably below 12 months of age. Hence, the nutritional composition is for feeding or is used for feeding a human subject. The present composition comprises a lipid, and preferably a protein and preferably a digestible carbohydrate component wherein the lipid component preferably provides 30 to 60% of total calories, the protein component preferably provides 5 to 20%, more preferably 5 to 15 wt. %, of the total calories and the digestible carbohydrate component preferably provides 25 to 75% of the total calories. Preferably the present composition comprises a lipid component providing 35 to 50% of the total calories, a protein component provides 6 to 12% of the total calories and a digestible carbohydrate component provides 40 to 60% of the total calories. The amount of total calories is determined by the sum of calories derived from protein, lipids and digestible carbohydrates.

The present composition is not human breast milk. The present composition comprises vegetable lipids. The compositions of the invention preferably comprise other fractions, such as vitamins, minerals according to international directives for infant formulae.

In one embodiment the composition is a powder suitable for making a liquid composition after reconstitution with an aqueous solution, preferably with water. Preferably the composition is a powder to be reconstituted with water. It was surprisingly found that the size and the coating with polar lipids of the lipid globules remained the same after the drying step and subsequent reconstitution.

In order to meet the caloric requirements of the infant, the composition preferably comprises 50 to 200 kcal/100 ml liquid, more preferably 60 to 90 kcal/100 ml liquid, even more preferably 60 to 75 kcal/100 ml liquid. This caloric density ensures an optimal ratio between water and calorie consumption. The osmolarity of the present composition is preferably between 150 and 420 mOsmol/l, more preferably 260 to 320 mOsmol/l. The low osmolarity aims to reduce the gastrointestinal stress. Stress can induce adipocyte formation.

Preferably the composition is in a liquid form, with a viscosity below 35 mPa·s, more preferably below 6 mPa·s as measured in a Brookfield viscometer at 20° C. at a shear rate of 100 s$^{-1}$. Suitably, the composition is in a powdered from, which can be reconstituted with water to form a liquid, or in a liquid concentrate form, which should be diluted with water. When the composition is in a liquid form, the preferred volume administered on a daily basis is in the range of about 80 to 2500 ml, more preferably about 450 to 1000 ml per day.

Infant

The composition of the present invention is preferably for use in infants. Because of the benefits for the developing child, it is advantageous to establish the present fatty acid programming effect of n3 and n6 (LC-)PUFA incorporation in brain membranes early in life. Hence the present composition is preferably administered to the human subject during the first 3 years of life. In one embodiment of the use according to the present invention, the nutritional composition is for feeding or is used for feeding a human subject with an age between 0 and 36 months. The present composition is advantageously administered to a human of 0-24 months, more preferably to a human of 0-18 months, most preferably to a human of 0-12 months.

Preferably the composition is to be used in infants which are prematurely born or which are small for gestational age. These infants experience after birth a catch up growth, which requires extra attention on proper fat handling. Preferably the composition is to be used in infants which are large for gestational age, since in these infants proper allocation of ingested fat is required.

Application

The present composition is preferably administered orally to the infant. The present invention is preferably considered to be of benefit for cognitive and/or behavioural performances at the age above 36 months and for the general condition of the brain later in life. In one embodiment the present method is for achieving the effects described herein when said human subject has an age above 36 months, preferably when said human subject has an age above 5 years, particularly above 13 years, more particularly above 18 years. In one embodiment the present method or the present nutritional composition is for feeding a human subject with an age between 0 and 36 months and for achieving the effects described herein when said human subject has an age above 36 months, preferably when said human subject has an age above 5 years, particularly above 13 years, more particularly above 18 years. In one embodiment the present method is for altering brain membrane fatty acid composition selected from the group consisting of increasing brain membrane fluidity, increasing brain membrane PUFA, increasing brain membrane LC-PUFA, increasing brain membrane n3 PUFA, increasing brain membrane n3 LC-PUFA, increasing brain membrane DHA of a human subject, decreasing the ratio of brain membrane n6/n3 (LC-)PUFA, amelioration of cognitive performance preferably memory performance and/or language development performance, more preferably learning memory performance, behavioural performance, visual acuity and fine motor skills, in a human subject, when said human subject has an age above 36 months, preferably when said human subject has an age above 5 years, particularly above 13 years, more particularly above 18 years. In one embodiment the present method or the present nutritional composition is for feeding a human subject with an age between 0 and 36 months and for altering brain membrane fatty acid composition selected from the group consisting of increasing brain membrane fluidity, increasing brain membrane PUFA, increasing brain membrane LC-PUFA, increasing brain membrane n3 PUFA, increasing brain membrane n3 LC-PUFA, increasing brain membrane DHA, decreasing ratio of n6/n3 brain membrane (LC-)PUFA of a human subject, amelioration of cognitive performance, preferably memory performance and/or language development performance, more preferably learning memory performance, behavioural performance, visual acuity and fine motor skills, in a human subject, when said human subject has an age above 36 months, preferably at the age above 5 years, particularly above 13 years, more particularly above 18 years. In one embodiment increasing brain membrane fluidity, increasing brain membrane PUFA, increasing brain membrane LC-PUFA, increasing brain membrane n3 PUFA, increasing brain membrane n3 LC-PUFA, increasing brain membrane DHA, decreasing ration of barin membrane n6/n3 (LC-)PUFA and amelioration of cognitive performance preferably memory performance and/or language development performance, more preferably learning memory performance, behavioural performance, visual acuity, fine motor skills occurs later in life. With later in life is meant an age exceeding the age at which the diet is taken, preferably with at least one year.

Cognitive performance in the present invention refers preferably to any one selected from the group consisting of memory (such as short term memory, long term memory) performance, learning capacity, alertness, attention, and concentration capacity, more preferably memory performance and/or language development performance, more preferably learning memory performance.

The inventors surprisingly found that when mice during infancy and childhood were fed a food composition comprising lipid globules coated with polar lipids, a different and significant effect on brain membrane composition later in life was observed compared to mice which during infancy and childhood had been fed a food composition having a similar fatty acid composition, but no polar lipids, in particular present in the form of a coating. At day 42, which is a time point corresponding to childhood in a human setting, no significant differences were observed in growth (weight) between the groups, but from day 42 both groups were fed a Western style diet which was high in fat. Surprisingly at day 98, which is a time point corresponding to early adulthood in humans, the mice, which had previously consumed the food composition of the present invention before turning to the Western style diet, had a significantly increased amount of brain membrane PUFA, LC-PUFA, and DHA than mice which had received a control composition. Consequently, the present finding can be put to use for prevention and/or treatment of a disorder associated with decreased brain membrane fluidity and/or associated with decreased brain membrane PUFA content and/or LC-PUFA content or increased ratio n6/n3 PUFA. More in particular, the present finding can be put to use for prevention and/or treatment of a psychiatric, psychological and/or neurobiological disorder. Specific effects the present finding which can be expected more early in life reside in the amelioration of visual acuity and/or fine motor skills. Also the present finding is of benefit for amelioration of cognitive performance and/or behavioural performance. To even further specify the benefits of the present finding of an for altered fat handling, ultimately resulting in improved fatty acid availability especially in brain cell membranes, the present invention is for the treatment and/or prevention of attention deficiency, attention deficit hyperactivity disorder (ADHD), dyslexia, autism, depression, bipolar depression, anxiety, schizophrenia, obsessive compulsive disorder (OCD), bulimia, abuse of alcohol or drugs, borderline personality disorder, panic disorder, social phobia, learning difficulties, mild cognitive impairment learning memory impairment, language development impairment, dementia, Alzheimer's disease and Parkinson's disease. As a non-optimal brain fatty acid composition is considered to be very important for developing ADHD, dyslexia and autism, the present invention is preferably for the treatment and/or prevention of one selected from the group consisting of ADHD, dyslexia and, autism. As a non-optimal brain fatty acid composition is considered to be very important for developing mild cognitive impairment, learning memory impairment, dementia, Alzheimer's disease and Parkinson's disease the present invention is preferably for the treatment and/or prevention of one selected from the group consisting of mild cognitive impairment learning memory impairment, Alzheimer's disease and Parkinson's disease more preferably learning memory impairment. The inventors proved this concept by demonstrating an improved performance in the Morris watermaze tasks by rats having consumed the nutritional composition of the present invention.

Though the nutritional composition is in particular suitable for infants, because of the long term effects and the enhanced plasticity of the brain during infancy, the nutritional composition is also suitable for other human subjects. It is believed that also later in life the brain membrane fatty acid composition can be adapted. Direct diet effects on brain membrane fatty acid composition were already observed after 5 days of administration of the diet of the present invention. Therefore in a preferred embodiment the present nutritional composition can also be used in other human subjects, preferably patients suffering from one of the disorders mentioned above and/or elderly. Elderly in the present invention are defined as humans with an age of 50 or above, more preferably 60 or above, even more preferably 65 or above.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

Example 1

Process for Preparing an IMF with Lipid Globules Differing in Architecture

An infant formula was prepared comprising per kg powder about 4800 kcal, 248 g lipid, 540 g digestible carbohydrates, 55 g non-digestible oligosaccharides and 103 g protein.

The composition was prepared using, a vegetable oil blend, demineralised whey powder, lactose, non-digestible oligosaccharides (galacto-oligosaccharides and long chain fructo-oligosaccharides in a weight ratio of 9/1). Vitamins, minerals, and trace elements as known in the art were used. For diet 3 to 6 also a butter milk serum powder comprising polar lipids from milk origin was used. An aqueous phase was prepared mixing all components, besides inulin and the oil blend and for diet 3 and 5 also the butter milk serum, in water, at room temperature, by stirring. Potassium hydroxide was used to set the pH at 6.8-7.0. The dry weight matter of the mixture was about 27%. The mixture was heated to 60° C. The vegetable oil blend was also heated to 60° C. and added to the water phase and blended with an Ultra-Turrax T50 for about 30-60 s at 5000-10000 rpm.

Subsequently the oil-water mixture was homogenised at a pressure of 100 bar in a first step and 50 bar in a second step in a Niro Suavi NS 2006 H Homogenizer for diet 1, 3 and 5. For diet 2 and 3 and 4 this mixture was homogenized in two steps at a pressure of 5 and 20 bar, respectively. The temperature was 60° C. The product was UHT treated at 125° C. for 30 s. The product was dried to a powder by spray drying. Long chain inulin was blended dry into the powder. For diet 3 and 4 also butter milk serum powder was dry blended into the powder.

The amount of vegetable glycerophospholipids was 0.2 wt. % based on total fat for diet 1 and 2. Diet 1 and 2 did not contain sphingolipids and cholesterol. Diet 3 and 4 comprised about 1.83 wt. % glycerophospholipids based on total fat, of which about 90% derived from the butter milk powder and about 10% already present in the standard IMF derived from vegetable oils, and further comprised milk derived sphingolipids of which the majority (about 0.47 wt. % based on total fat) was sphingomyelin; the rest being glycosphingolipids. Diet 3 and 4 comprised about 0.05 wt. % milk derived cholesterol based on total fat. Diet 5 and 6 comprised half of the amount of milk derived polar lipids based on total fat of diet 3 and 4.

The size of the lipid globules was measured with a Mastersizer 20000 (Malvern Instruments, Malvern UK) and shown in Table 1. Coating of the lipid globules with polar lipids in diet 5 and 6 and absence of coating in diet 1, 2, 3 and 4 was confirmed by confocal laser scanning microscopy method. It was checked with confocal laser scanning microscopy that the larger lipid globules of the present invention were coated with phospholipids, before spray drying and after reconstitution of the spray dried powder with water. In both cases the lipid globules of diet 4 and 6 were covered with a layer of phospholipids. As fluorescent probes Annexin V Alexa Fluor 488 (In Vitrogen molecular probes) for labeling the phospholipids, and Nile Red (Sigma-Aldrich) for labeling triglycerides, were used. After labeling the milk samples Vectrashield mounting medium (Vector laboratories inc., Burliname USA) for reducing particle movement and photo-bleaching was added. Observations were made using a Zeiss Laser Scanning Microscope with excitation wavelengths of 488/543/633 nm and emission filters set at band pass 505-530, and band pass 560-615. Also the size of the lipid globules was the same before drying and after reconstitution of the spray dried powder with water.

TABLE 1

Lipid globule characteristics of different milks

| IMF | Volume Mode diameter μm | Volume % with a diameter between 2 and 12 μm |
|---|---|---|
| 1, Standard IMF (small lipid globules) | 0.5 | 5.1 |
| 2, Experimental IMF (large lipid globules) | 4.0 | 72.2 |
| 3, Experimental IMF (small lipid globules, free polar lipids) | 0.4 | 3.9 |
| 4, Experimental IMF (large lipid globules, free polar lipids) | 5.0 | 74.8 |
| 5, Experimental IMF (small lipid globules, coated with polar lipids) | 0.5 | 4.3 |
| 6, Experimental IMF (large lipid globules, coated with polar lipids | 4.3 | 70.3 |

After 5 months storage at room temperature the size of the lipid globules in diet 1, 3 and 5 had not changed, with a volume mode diameter of 0.5, 0.4 and 0.5 respectively. Also the volume mode diameter of diet 2, 4 and 6 were rather stable being 4.8 μm, 7.9 μm and 6.6 μm, respectively.

Example 2

Offspring of C57/BL6 dams were weaned from day 15 on. The experimental weaning diets were continued until day 42. From day 42 to day 98 all pups were ad libitum fed the same diet based on AIN-93G diet with an adjusted lipid fraction (containing 10 wt. % lipid of which 50 wt. % lard and 1% cholesterol, based on total lipid), which is representative for a Western style diet.

The experimental diets that were used for weaning were:
1) an infant milk formula (IMF) based control diet. This diet comprised 282 g standard IMF (IMF 1 of example 1) per kg, with the lipid globule size as mentioned in example 1. The rest of the diet was AIN-93G protein, carbohydrates and fibre. All lipid present in the diet was derived from the IMF.
2) an IMF based experimental diet. This diet comprised 282 g experimental IMF (IMF 2 of example 1) per kg, with the lipid globule size as mentioned in example 1. The rest of the diet was AIN-93G protein, carbohydrates and fibre. All lipid present in the diet was derived from the IMF.
3) an IMF based experimental diet. This diet comprised 282 g experimental IMF (IMF 3 of example 1) per kg, with the lipid globule size as mentioned in example 1 and comprising phospholipids in free form. The rest of the diet was AIN-93G protein, carbohydrates and fibre. All lipid present in the diet was derived from the IMF.
4) an IMF based experimental diet. This diet comprised 282 g experimental IMF (IMF 4 of example 1) per kg, with the lipid globule size as mentioned in example 1 and comprising phospholipids in free form. The rest of the diet was AIN-93G protein, carbohydrates and fibre. All lipid present in the diet was derived from the IMF.
5) an IMF based experimental diet. This diet comprised 282 g experimental IMF (IMF 5 of example 1) per kg, with the lipid globule size as mentioned in example 1 and with phospholipids present as a coating around the lipid globules. The rest of the diet was AIN-93G protein, carbohydrates and fibre. All lipid present in the diet was derived from the IMF.
6) an IMF based experimental diet. This diet comprised 282 g experimental IMF (IMF 6 of example 1) per kg, with the lipid globule size as mentioned in example 1 and with phospholipids present as coating around the lipid globules. The rest of the diet was AIN-93G protein, carbohydrates and fibre. All lipid present in the diet was derived from the IMF.

At day 42, all mice switched to a "Western style diet" comprising 4016 kJ per 100 g, 10 wt. % lipid, 1 wt % cholesterol based on total fat, 60 wt % digestible carbohydrates, 4.75 wt. % fibers, and 17.9 wt. % protein, until day 98.

The fatty acid composition of the experimental diets was very similar in respect of saturated, mono-unsaturated, poly unsaturated and long chain poly unsaturated fatty acids, with calculated linoleic acid (LA) of 14 wt % in diet 1 and 2, and 13.2 wt % in diet 3, 4, 5 and 6, based on total fatty acids, with alpha-linoleic acid (ALA) of 2.6 wt. % in diet 1 and 2 and 2.5 wt % in diet 3, 4, 5 and 6, based on total fatty acids and with LA/ALA ratio of 5.4 in diet 1 and 2 and 5.3 in diet 3, 4, 5 and 6, respectively. The amount of DHA was 0.2 wt. % in all 6 diets, and the amount of ARA was 0.35 wt. % in diet 1 and 2 and 0.36 wt. % in diet 3, 4, 5 and 6. In the Western style diet the amount of LA was 11.9 wt. %, the amount of ALA was 1.3 wt. %, based on total fatty acids and the ratio LA/ALA was 9.15.

The mice were weighed twice a week. The food intake was determined once a week during the entire experiment. To determine body composition (i.e., fat mass (FM) and fat-free mass (FFM)) DEXA scans (Dual Energy X-ray Absorbiometry) were performed under general anesthesia at 6, 10 and 14 weeks of age, 42, 70, and 98 days after birth respectively, by densitometry using a PIXImus imager (GE Lunar, Madison, Wis., USA). At the age of 98 days the male mice were sacrificed and organs including brains were dissected and weighed. Of each brain, 1 hemisphere was homogenized (Utra-Turrax T25 basic, IKA, VWR international) in 50 volumes of ice cold deionized water (MiliQ). Subsequently, brain fatty acid (FA) profile was quantified by means of gas chromatographic analysis. 1 ml brain homogenate was extracted according to the procedure of Bligh & Dyer (dichloromethane/methanol extraction). The lipids were converted into methyl esters with concentrated sulfuric acid in methanol. The fatty acid methyl esters (FAME) were extracted from the methanol solution with hexane and analyzed on a gas chromatograph (GC) equipped with a flame ionization detector (FID).

Results:

At day 98, the FA profile of the brains was determined. Table 2 shows the general FA profile of the brains (SFA, MUFA, PUFA, LCPUFA, n3, n6, n6/n3-ratio, n3 LC-PUFA, n6 LC-PUFA, n6/n3 LC-PUFA ratio) and Table 3 shows the profile of specific LC-PUFA's (DHA, EPA, ARA, ALA, C22:4 n6, C22:5 n-3 and C22:5 n-6).

When differences between individual programming diets were compared, no effects of programming diet were found on % SFA and % MUFA, but the % of all other parameters in the FA profile were affected; PUFA, LC-PUFA, n6 PUFA's, n3 PUFA's, n6/n3 PUFA ratio, n6 LC-PUFA's, n3 LC-PUFA's, and n6/n3 LC-PUFA ratio. Many of these effects were related to the somewhat different brain FA profile of animals that were raised on the large lipid globule diet without phospholipids (diet 2) compared to the other diets. Diet 2 resulted in lower PUFA, LC-PUFA, n6 PUFA, n3 PUFA, n6 and n3 LC-PUFA than the other diets ($p<0.05$).

TABLE 2

Fatty acid composition of brain membranes later in life after an early diet with different lipid globules

| | Diet | | | | | |
|---|---|---|---|---|---|---|
| | Diet 1 Small lipid globules | Diet 2 Large lipid globules | Diet 3 Small lipid globules, free polar lipids | Diet 4 Large lipid globules, free polar lipids | Diet 5 Small lipid globules, coated with polar lipids | Diet 6 Large lipid globules, coated with polar lipids |
| SFA | 40.23 ± 0.39 | 41.17 ± 0.46 | 40.43 ± 0.50 | 40.06 ± 0.48 | 40.25 ± 0.42 | 40.06 ± 0.35 |
| MUFA | 24.25 ± 0.37 | 25.09 ± 0.44 | 24.11 ± 0.40 | 24.91 ± 0.37 | 24.31 ± 0.61 | 23.81 ± 0.54 |
| PUFA | 25.79 ± 0.17 | 24.59 ± 0.38 | 26.02 ± 0.33 | 25.59 ± 0.23 | 25.75 ± 0.56 | 26.34 ± 0.35 |
| LC-PUFA | 24.53 ± 0.19 | 23.40 ± 0.39 | 24.92 ± 0.34 | 24.42 ± 0.24 | 24.61 ± 0.58 | 25.16 ± 0.38 |

TABLE 2-continued

Fatty acid composition of brain membranes later in life after an early diet with different lipid globules

| | Diet | | | | | |
|---|---|---|---|---|---|---|
| | Diet 1 Small lipid globules | Diet 2 Large lipid globules | Diet 3 Small lipid globules, free polar lipids | Diet 4 Large lipid globules, free polar lipids | Diet 5 Small lipid globules, coated with polar lipids | Diet 6 Large lipid globules, coated with polar lipids |
| n6 | 11.29 ± 0.13 | 10.89 ± 0.12 | 11.53 ± 0.16 | 11.19 ± 0.12 | 11.34 ± 0.19 | 11.48 ± 0.20 |
| n3 | 14.40 ± 0.10 | 13.59 ± 0.28 | 14.24 ± 0.22 | 14.18 ± 0.14 | 14.19 ± 0.28 | 14.64 ± 0.17 |
| n6/n3 | 0.78 ± 0.010 | 0.80 ± 0.011 | 0.81 ± 0.013 | 0.79 ± 0.008 | 0.80 ± 0.009 | 0.78 ± 0.010 |
| n6 LC | 10.60 ± 0.11 | 10.30 ± 0.12 | 10.99 ± 0.15 | 10.61 ± 0.12 | 10.77 ± 0.27 | 10.84 ± 0.21 |
| n3 LC | 13.83 ± 0.12 | 12.99 ± 0.29 | 13.70 ± 0.24 | 13.59 ± 0.15 | 13.63 ± 0.30 | 14.10 ± 0.20 |
| n6/n3 LC | 0.77 ± 0.007 | 0.80 ± 0.012 | 0.80 ± 0.014 | 0.78 ± 0.007 | 0.79 ± 0.007 | 0.77 ± 0.010 |

Furthermore, the n6/n3 ratio in the brains of diet 3 fed animals was higher than diet 1 (p=0.043) (PL effect) and diet 4 (p=0.083) (size effect). The n6/n3 LC-PUFA ratio was higher in the brains of the animals that received the diet 5 diet compared to diet 1 (p=0.082) (PLcoating effect) and the diet 6 (p=0.093) (size effect).

of EPA was lower in the diet 1 group than in the diet 3 group (z=−1.815, p=0.069 TREND), diet 4 group (p=0.033), diet 5 group (p=0.029) and diet 6 group (p=0.074 trend) group. There was also a difference in the % of EPA between the diet 2 group and diet 4 group (p=0.050), these effects emphasize the previously described effect of PL in the diet on EPA.

TABLE 3

| | Diet | | | | | |
|---|---|---|---|---|---|---|
| | Diet 1 Small lipid globules | Diet 2 Large lipid globules | Diet 3 Small lipid globules, free polar lipids | Diet 4 Large lipid globules, free polar lipids | Diet 5 Small lipid globules, coated with polar lipids | Diet 6 Large lipid globules, coated with polar lipids |
| C18:3 n3 (ALA) | 0.47 ± 0.02 | 0.49 ± 0.02 | 0.45 ± 0.02 | 0.48 ± 0.02 | 0.46 ± 0.03 | 0.44 ± 0.03 |
| C18:2 n6 LA | | | | | | |
| C20:4 n6 (ARA) | 7.62 ± 0.12 | 7.40 ± 0.12 | 7.86 ± 0.13 | 7.58 ± 0.11 | 7.66 ± 0.22 | 7.71 ± 0.18 |
| C20:5 n3 (EPA) | 0.006 ± 0.003 | 0.006 ± 0.003 | 0.021 ± 0.008 | 0.032 ± 0.011 | 0.023 ± 0.007 | 0.016 ± 0.005 |
| C22:6 n3 (DHA) | 13.40 ± 0.13 | 12.52 ± 0.30 | 13.25 ± 0.24 | 13.08 ± 0.15 | 13.17 ± 0.32 | 13.64 ± 0.12 |
| C22:4 n6 (DTA) | 2.22 ± 0.03 | 2.20 ± 0.02 | 2.30 ± 0.03 | 2.23 ± 0.02 | 2.29 ± 0.04 | 2.23 ± 0.04 |
| C22:5 n6 ("DPA") | 0.04 ± 0.01 | 0.05 ± 0.01 | 0.19 ± 0.01 | 0.17 ± 0.02 | 0.17 ± 0.01 | 0.17 ± 0.01 |
| C22:5 n3 (DPA) | 0.14 ± 0.019 | 0.16 ± 0.006 | 0.15 ± 0.008 | 0.16 ± 0.004 | 0.15 ± 0.005 | 0.17 ± 0.005 |

The % of the specific LCPUFA's DHA, EPA, ARA, ALA, C22:4 n-6, C22:5 n-3 and C22:5 n-6 is depicted in Table 3. LA was not detected in the brain.

There was no effect of programming diet on % of ALA, ARA and C22:5 n3. The % of C22:5 n6 was affected by programming diet (p<0.001), the % of C22:5 n6 was lower in the diet 1 and diet 2 groups than in the groups with diet 3-6 (p<0.001), which emphasizes that adding PL to the diet results in higher % C22:5 n6. There was also an effect of programming diet on % of C22:4 n6 (p=0.003), the % of C22:4 n6 was higher in animals from the diet 3 group than from the diet 1 group (p=0.059 trend) and diet 4 group (p=0.061 TREND). The % of DHA was affected by diet as well (p=0.038), the % of DHA in the brains of animals in the diet 2 group was lower than that of diet 1 (p=0.008), diet 4 (p=0.086, trend) and diet 6 (p=0.001), the diet 6 group was also higher than diet 4 (p=0.091, trend). For the % of EPA, a significant effect of diet was also present (p=0.050), the %

In a strategy to use large lipid globules for achieving an effect on obesity later in life, it was found that brain membrane fatty acid composition was not improved compared to standard infant milk formula. Also standard IMF in terms of lipid globule size wherein the lipid globules had a phospholipid coating showed no improvement in brain membrane fatty acid composition. However, only in the case of using large lipid globules, coated with phospholipids or polar lipids, an improvement in brain membrane fatty acid composition in terms of (LC-)PUFA content was observed, while the advantageous effect on obesity later in life was also achieved as well as the advantageous effect on bone mineral accretion.

Thus advantageously the diet with large lipid globules coated with phospholipids and/or polar lipids further showed strong improved effects on long term effects of obesity, visceral adiposity, lean body mass, bone mineral content and bone mineral density compared with a diet comprising small lipid globules covered mainly with protein.

Overall, the FA profile in the brains of mice exposed early in life to diet 6 with large lipid globules coated with polar lipids, was the best with the highest % of PUFA (both n3 and n6) and LC-PUFA (both n3 and n6), and thus an improved fluidity, and a relatively low n6/n3 PUFA and low n6/n3 LC-PUFA ratio. These effects were especially prominent compared to large lipids without PL (diet 2). A diet with large lipid globules with free PL (diet 4) showed intermediate effects, indicating that the location of the PL as a coating around the lipid globule plays a role. When small lipid globules were used these effects were much less clear. No effect of free PL and coating was observed with free PL or PL coating in small lipid globules and due to slightly increased n6 (LC)-PUFA in the presence of PL n6/n3 (LC)-PUFA ratios were slightly increased in the presence of PL, which is not desired. Furthermore, of the n3-PUFA in diet group 6 beneficially had the highest amount of DHA and DPA, with relatively lower amounts of EPA and ALA. It can be concluded that both the lipid globules have to be increased in size and they have to be surrounded by a coating comprising phospholipids in order to see improved long term effect on brain FA composition compared to lipid globules as present in standard IMF.

Example 3

Effect of Different Dietary Lipid Globules on Long Term Fatty Acid Composition of Brain Membranes The experiment of example 2 was repeated in a similar way. Difference in lipid globule size was obtained by a difference in homogenization pressure as described in example 1. The pressure of homogenization was 10/5 for diet 2, 4 and 6 and 550/50 for diet 1, 3, and 5. The volume mode diameter of the lipid globules of diet 1, 3, and 5 ranged from 0.23 to 0.28 µm. Less than 10 vol. % had a diameter between 2 and 12 µm. The volume mode diameter of the lipid globules in diet 2, 4 and 5 ranged from 3.0 to 4.4 µm. More than 50 vol. % had a diameter between 2 and 12 µm. The source of phospholipids for diet 3 to 6 was SM2 powder from Corman which was used at a final concentration of about 1.3% phospholipid based on total lipid. Diets were similar as in example 2, except for the Western style diet, which was more unhealthy, comprising 4520 kJ per 100 g, 20 wt. % lipid, 1 wt % cholesterol based on total fat, 52 wt % digestible carbohydrates, 4.75 wt. % fibers, and 17.9 wt. % protein, until day 98.

The fatty acid composition of the experimental diets was very similar in respect of saturated, mono-unsaturated, poly unsaturated and long chain poly-unsaturated fatty acids and similar to example 2.

At the age of 98 days the brain membrane fatty acid composition was determined as in example 2. Also on day 98 blood samples were taken and the fatty acid composition of the red blood cell membranes was determined.
Results:

At day 98, the fatty acid profile of the brains was determined. Table 4 shows the general fatty acid profile of the brains and shows the profile of the major LC-PUFA.

TABLE 4

Fatty acid composition of brain membranes later in life after an early diet with different lipid globules

| | Diet | | |
|---|---|---|---|
| | Diet 1 Small lipid globules | Diet 5 Small lipid globules, coated with polar lipids | Diet 6 Large lipid globules, coated with polar lipids |
| PUFA | 26.66 (0.15) | 26.86 (0.19) | 26.98 (0.22) |
| LC-PUFA | 25.51 (0.16) | 25.74 (0.21) | 25.88 (0.23) |
| n6 | 12.15 (0.07) | 12.29 (0.10) | 12.25 (0.13) |
| n3 | 14.42 (0.12) | 14.48 (0.12) | 14.64 (0.13) |
| n6/n3 | 0.843 (0.01) | 0.849 (0.01) | 0.837 (0.01) |
| n6 LC | 11.60 (0.06) | 11.75 (0.10) | 11.72 (0.13) |
| n3 LC | 13.82 (0.13) | 13.90 (0.13) | 14.08 (0.14) |
| n6/n3 LC | 0.840 (0.01) | 0.846 (0.01) | 0.833 (0.01) |
| C20:4 n6 (ARA) | 8.21 (0.07) | 8.34 (0.09) | 8.33 (0.11) |
| C22:6 n3 (DHA) | 13.36 (0.14) | 13.45 (0.14) | 13.64 (0.15) |
| C22:4 n6 (DTA) | 2.42 (0.02) | 2.42 (0.02) | 2.41 (0.04) |

When differences between individual diets were compared, the amount of PUFA, LC-PUFA, n6 PUFA's, n3 PUFA's, n6 LC-PUFA's, n3 LC-PUFA's was increased in diet 5 and 6 (small and large, phospholipid coated lipid globules), with diet 6 having the most improved effects on increase of PUFA, LC-PUFA, n3 PUFA and n3-LC-PUFA. Additionally the ratio of n6/n3 PUFA and n6/n3 LC-PUFA was beneficially decreased most in diet 6. An increase in DHA and ARA is observed in diet 5 and 6. The amount of DHA in diet 6 is beneficially even further increased compared to diet 5.

No effect in fatty acid composition of the red blood cell membranes was observed (data not shown). Since the fatty acid composition is a reflection of the fatty acid composition in the diet, this is indicative for the specific long term effects of early diet on brain membrane composition. This effect is still present even after a long period on a less healthy diet with low LC-PUFA and a high n6/n3 PUFA ratio.

Example 4

Direct Diet Effects with Different Lipid Globules on Fatty Acid Composition of Brain Membranes Mice and diets similar to example 2 were used. The diets were administered from day 15 to day 28. On day 28 the fatty acid composition of the brain membranes was determined, similar as in example 2.

In this experiment the direct diet effects on brain membrane fatty acid composition was determined. The diet was similar as in example 2. As a source of phospholipids 80% butter milk serum (Cormann SN2), and 20% soy lecithin was used. The amount of phospholipids added based on total fat was 2.9 wt. %

The volume mode diameter of the lipid globules of diet 1, 3, and 5 ranged from 0.49 to 0.60 µm. Less than 5 vol. % had a diameter between 2 and 12 µm. The volume mode diameter of the lipid globules in diet 2, 4 and 5 ranged from 4.4 to 7.9 µm. More than 55 vol. % had a diameter between 2 and 12 µm.

The results on brain membrane fatty acid composition are shown in are shown in table 5.

TABLE 5

Fatty acid composition of brain membranes after
a diet with different lipid globules

| | Diet | | | |
|---|---|---|---|---|
| | Diet 1<br>Small lipid<br>globules | Diet 3<br>Small lipid<br>globules, free<br>polar lipids | Diet 5<br>Small lipid<br>globules,<br>coated<br>with polar<br>lipids | Diet 6<br>Large lipid<br>globules,<br>coated<br>with polar<br>lipids |
| PUFA | 27.73 (0.20) | 27.86 (0.14) | 27.89 (0.18) | 27.68 (0.16) |
| LC-PUFA | 26.71 (0.22) | 26.91 (0.17) | 26.86 (0.19) | 26.69 (0.19) |
| n6 | 13.80 (0.11) | 13.63 (0.10) | 13.56 (0.14) | 13.41 (0.11) |
| n3 | 13.85 (0.15) | 14.15 (0.10) | 14.22 (0.08) | 14.19 (0.10) |
| n6/n3 | 1.00 (0.01) | 0.963 (0.01) | 0.954 (0.01) | 0.945 (0.01) |
| n6 LC | 13.25 (0.12) | 13.12 (0.10) | 13.02 (0.15) | 12.90 (0.12) |
| n3 LC | 13.38 (0.16) | 13.70 (0.11) | 13.75 (0.09) | 13.71 (0.11) |
| n6/n3 LC | 0.99 (0.01) | 0.96 (0.01) | 0.95 (0.01) | 0.94 (0.01) |
| DHA | 12.94 (0.18) | 13.31 (0.11) | 13.33 (0.09) | 13.22 (0.12) |
| ARA | 9.45 (0.11) | 9.40 (0.10) | 9.27 (0.13) | 9.25 (0.13) |
| DTA | 2.40 (0.03) | 2.37 (0.03) | 2.32 (0.03) | 2.29 (0.02) |

As can be deduced from the results, fatty acid composition in brain membranes was improved after consumption of a diet with lipid globules were coated with phospholipids, see effects of diet 5 versus diet 1 on increase in (LC-)PUFA, DHA and decrease in ARA and n6/3 ratio of (LC) PUFA. This effect was less, when the phospholipids were separately present, not in the form of a coating (see diet 3). This is an indication that the phospholipids should be present in the coating of the lipid globule. This effect was further improved using large coated lipid globules (diet 6 versus diet 5). This is an indication that the coated lipid globules should preferably be large.

Example 5

Direct Diet Effects of Different Lipid Globules of on Fatty Acid Composition of Brain Membranes Diet 1 and 6 similar to example 2, 3 and 4 were consumed for 5 days by Wistar rat pups (day 16-21 after birth). The amount of phospholipids was 1.6 wt. % based on total fat. As a source of phospholipids butter milk powder was used. The mode diameter of the lipid globules in diet 1 was 0.5 μm and of diet 6 3.0 μm.

The membrane fatty acid composition of the brain was determined as in example 2. The results are shown in Table 6.

TABLE 6

Fatty acid composition of brain membranes after
5 days of a diet with different lipid globules

| | Diet 1<br>Small uncoated<br>lipid globules | Diet 6<br>Large coated<br>lipid globules |
|---|---|---|
| PUFA | 30.48 (0.26) | 30.53 (0.18) |
| LC-PUFA | 29.13 (0.26) | 29.15 (0.18) |
| n6 PUFA | 17.45 (0.22) | 17.22 (0.10) |
| n3 PUFA | 12.98 (0.17) | 13.26 (0.09) |
| n6/n3 PUFA | 1.35 (0.03) | 1.30 (0.01)* |
| n6 LC-PUFA | 16.45 (0.21) | 16.17 (0.10) |
| n3 LC-PUFA | 12.64 (0.17) | 12.92 (0.09) |
| n6/n3 LC-PUFA | 1.30 (0.03) | 1.25 (0.01)** |
| DHA | 12.27 (0.17) | 12.56 (0.10)* |
| ARA | 11.08 (0.13) | 10.83 (0.09) |
| DTA | 3.41 (0.06) | 3.33 (0.04) |

*$p > 0.1$,
**$p > 0.05$

As can be deduced from the results, even after 5 days consumption of the nutritional composition of the present invention an improved effect was observed on (LC-)PUFA, DHA, and n6/n3 (LC)-PUFA ratio in brain membranes. The amount of n6 (LC-)PUFA advantageously decreased.

Example 6

Effect on Cognitive Performance of a Diet with Different Lipid Globules

The same diet of example 4 was used. This diet was given to Wistar rats. The male rats consumed the feed from day 16 to day 42. On day 42 the male rats were submitted to a a short version of the Morris water maze test. Morris water maze tests, also known as Morris water navigation tasks, are widely used in the art of behavioral neuroscience, and is a behavioral procedure to study cognitive function, in particular spatial learning and memory. In this experiment the animals were trained to locate a hidden platform based on environmental cues. In short a platform was submerged just below water surface at a fixed position in a round water tank. The tank was in a room with fixed cues on the walls that were visible from the water surface in the tank. Animals were allowed to sit on the submerged platform for 60 seconds to get acquainted with the environment. Directly after that, animals were placed in the water tank and had to locate the submerged platform within 60 seconds. Animals were trained in 4 successive trials with a different start-location each trial. The start location per trial was similar for all animals. Time to locate the platform per trial was measured. The results are shown in Table 7.

TABLE 7

Time to reach the platform in Morris water maze task (latency in seconds).

| diet | trial 1 | trial 2 | trial 3 | trial 4 | average |
|---|---|---|---|---|---|
| Diet 1 | 50.09 ± 5.21 | 40.97 ± 8.78 | 30.15 ± 8.91 | 28.88 ± 5.43 | 37.52 ± 3.50 |
| Diet 6 | 54.05 ± 3.93 | 27.97 ± 6.40 | 28.71 ± 8.68 | 24.98 ± 8.19 | 33.92 ± 3.49 |

As can be deduced from table 7, the performance is improved in rats having consumed the composition of the present invention. Especially prominent was the learning curve, which was much steeper when a diet of the present invention is consumed. This is indicative for an improved cognitive performance, in particular memory performance, more particular learning memory performance, memory and spatial learning.

The invention claimed is:

1. A method for increasing brain membrane n3 LC-PUFA and/or brain membrane DHA in a human subject, the method comprising administering to the human subject 80 to 2500 ml daily for at least 5 days a nutritional composition comprising:
   (a) 10 to 50 wt. % vegetable lipids based on dry weight of the composition,
   (b) 0.5 to 10 wt. % phospholipids based on total lipid,
   (c) glycosphingolipids and
   (d) cholesterol,
   wherein the composition comprises lipid globules with a core comprising the vegetable lipids and a coating comprising the phospholipids, the lipid globules having:
      (i) a volume-weighted mode diameter between 1.0 and 10 µm, and/or
      (ii) a diameter of 2 to 12 µm in an amount of at least 45 volume % based on total lipid,
   wherein the core comprises at least 90 wt. % triglycerides having fatty acids and the composition comprises glycerophospholipids having fatty acids derived from milk, and
   wherein the composition comprises linoleic acid (LA) in an amount between 5 and 15 wt. % based on total fatty acid.

2. The method according to claim 1, wherein the lipid globules have a diameter of 2 to 12 µm in an amount of at least 55 volume % based on total lipid.

3. The method according to claim 2, wherein the lipid globules have:
   (i) a volume-weighted mode diameter between 3.0 and 8.0 µm, and/or
   (ii) a diameter of 2 to 12 µm in an amount of at least 65 volume % based on total lipid.

4. The method according to claim 1, wherein the composition comprises n3 LC-PUFA in an amount of 0.2 to 15 wt. % based on total fatty acid.

5. The method according to claim 1, wherein the composition comprises DHA in an amount of 0.1 to 0.6 wt. % based on total fatty acid.

6. The method according to claim 1, wherein the composition comprises n6 LC-PUFA in an amount of 0.02 to 5 wt. % based on total fatty acid.

7. The method according to claim 1, wherein the composition comprises ARA in an amount of 0.1 to 0.6 wt. % based on total fatty acid.

8. The method according to claim 1, wherein the nutritional composition comprises linoleic acid (LA) and alpha-linolenic acid (ALA) in a weight ratio LA:ALA between 4:1 and 7:1.

9. The method according to claim 1, wherein brain membrane fluidity is increased.

10. A method for amelioration of cognitive performance in a human subject above 36 months of age, the method comprising administering to the human subject at an age between 0 and 36 months 80 to 2500 ml daily for at least 5 days a nutritional composition comprising:
   (a) 10 to 50 wt. % vegetable lipids based on dry weight of the composition,
   (b) 0.5 to 10 wt. % phospholipids based on total lipid,
   (c) glycosphingolipids and
   (d) cholesterol,
   wherein the composition comprises lipid globules with a core comprising the vegetable lipids and a coating comprising the phospholipids, the lipid globules having:
      (i) a volume-weighted mode diameter between 1.0 and 10 µm, and/or
      (ii) a diameter of 2 to 12 µm in an amount of at least 45 volume % based on total lipid,
   wherein the core comprises at least 90 wt. % triglycerides having fatty acids and the composition comprises glycerophospholipids having fatty acids derived from milk, and
   wherein the composition comprises linoleic acid (LA) in an amount between 5 and 15 wt. % based on total fatty acid.

11. The method according to claim 10, wherein the composition comprises n3 LC-PUFA in an amount of at least 0.2 wt. % based on total fatty acid and that does not exceed 15 wt. % based on total fatty acid.

12. The method according to claim 10, wherein the composition comprises DHA in an amount of 0.1 to 0.6 wt. % based on total fatty acid.

13. The method according to claim 10, wherein the composition comprises n6 LC-PUFA in an amount of at least 0.02 wt. % based on total fatty acid and that does not exceed 5 wt. % based on total fatty acid.

14. The method according to claim 10, wherein the composition comprises ARA in an amount of 0.1 to 0.6 wt. % based on total fatty acid.

15. The method according to claim 10, wherein the nutritional composition comprises linoleic acid (LA) and alpha-linolenic acid (ALA) in a weight ratio LA:ALA between 4:1 and 7:1.

16. The method according to claim 1, wherein the administration occurs when the human subject is between 0 and 36 months of age.

17. The method according to claim 16, wherein the brain membrane n3 LC-PUFA and/or brain membrane DHA is increased when the human subject has reached an age above 36 months.

18. The method according to claim 17, wherein the brain membrane n3 LC-PUFA and/or brain membrane DHA is increased when the human subject has reached an age above 5 years.

19. The method according to claim 1 or 10, wherein all polar lipids are derived from milk, wherein polar lipids are the sum of phospholipids, glycosphingolipids and cholesterol.

20. The method according to claim 1 or 10, wherein the milk is milk of cows, mares, sheep, goats, buffalos, horses and/or camels.

21. The method according to claim 19, wherein the milk is milk of cows, mares, sheep, goats, buffalos, horses and/or camels.

22. The method according to claim 1 or 10, wherein the composition further comprises non-digestible oligosaccharides with a degree of polymerization between 2 and 250.

* * * * *